United States Patent
Seino et al.

(10) Patent No.: US 12,043,615 B2
(45) Date of Patent: Jul. 23, 2024

(54) FLUORINE-CONTAINING PYRIMIDINE COMPOUND AND METHOD FOR MANUFACTURING THE SAME

(71) Applicant: UNIMATEC CO., LTD., Tokyo (JP)

(72) Inventors: Junya Seino, Kitaibaraki (JP); Rie Aotsu, Kitaibaraki (JP); Keisuke Kokin, Kitaibaraki (JP)

(73) Assignee: UNIMATEC CO., LTD. (JP)

( * ) Notice: Subject to any disclaimer, the term of this patent is extended or adjusted under 35 U.S.C. 154(b) by 782 days.

(21) Appl. No.: 17/279,466

(22) PCT Filed: Nov. 28, 2019

(86) PCT No.: PCT/JP2019/046489
§ 371 (c)(1),
(2) Date: Mar. 24, 2021

(87) PCT Pub. No.: WO2020/116296
PCT Pub. Date: Jun. 11, 2020

(65) Prior Publication Data
US 2021/0403455 A1  Dec. 30, 2021

(30) Foreign Application Priority Data
Dec. 7, 2018  (JP) .................................. 2018-229889

(51) Int. Cl.
*C07D 403/04*  (2006.01)
*C07D 401/04*  (2006.01)

(52) U.S. Cl.
CPC ......... *C07D 403/04* (2013.01); *C07D 401/04* (2013.01)

(58) Field of Classification Search
CPC .............................. C07D 403/04; C07D 401/04
See application file for complete search history.

(56) References Cited

U.S. PATENT DOCUMENTS

| | | |
|---|---|---|
| 2008/0132522 A1 | 6/2008 | Rheinheimer et al. |
| 2009/0275590 A1 | 11/2009 | Guzzo et al. |

(Continued)

FOREIGN PATENT DOCUMENTS

| | | |
|---|---|---|
| CN | 101903351 A | 12/2010 |
| CN | 102695706 A | 9/2012 |

(Continued)

OTHER PUBLICATIONS

Written Opinion of the International Searching Authority issued in PCT/JP2019/046489, mailed Feb. 10, 2020 with English Translation (7 pages).

(Continued)

*Primary Examiner* — Laura L Stockton
(74) *Attorney, Agent, or Firm* — Harness, Dickey & Pierce, P.L.C.

(57) ABSTRACT

A fluorine-containing pyrimidine compound is provided represented by general formula (1), (2), (3), (4), (5), or (6) below.

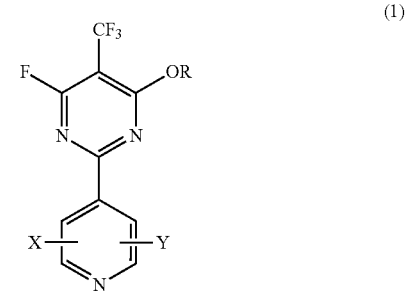

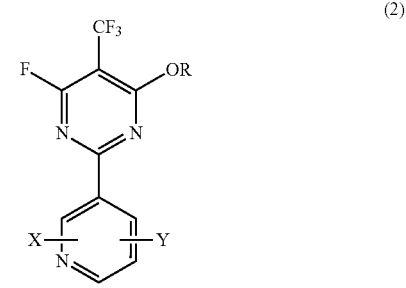

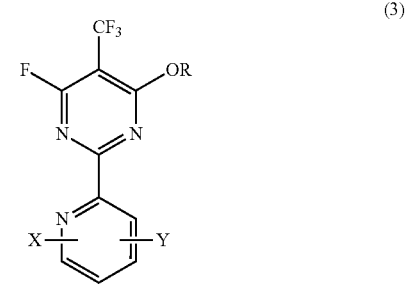

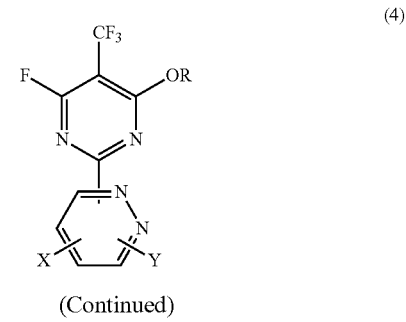

(Continued)

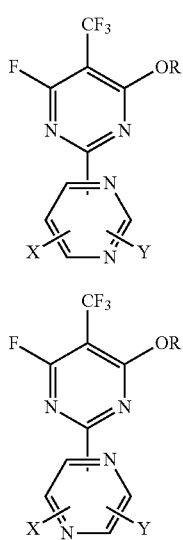

wherein, in the general formulae (1) to (6) above,

R represents a hydrocarbon group having 1 to 12 carbon atoms; and

X and Y each independently represent a hydrogen atom, a halogen atom, a hydrocarbon group having 1 to 10 carbon atoms, —$C_nF_{2n+1}$ (n is an integer of 1 to 10), a nitro group, a boronate group, —$OA^1$, —$SO_mA^1$ (m is an integer of 0 to 3), —$NA^1A^2$, —$COOA^1$, or —$CONA^1A^2$, and $A^1$ and $A^2$ each independently represent a hydrogen atom or a hydrocarbon group having 1 to 10 carbon atoms.

6 Claims, No Drawings

(56) References Cited

U.S. PATENT DOCUMENTS

| | | |
|---|---|---|
| 2010/0144760 A1 | 6/2010 | Alvaro et al. |
| 2011/0021486 A1 | 1/2011 | Beaulieu et al. |
| 2012/0214783 A1 | 8/2012 | Beaulieu et al. |
| 2013/0216498 A1 | 8/2013 | Eastwood et al. |
| 2013/0331391 A1 | 12/2013 | Beaulieu et al. |
| 2014/0206696 A1 | 7/2014 | Guzzo et al. |
| 2014/0221366 A1 | 8/2014 | Heinrich et al. |
| 2016/0157489 A1 | 6/2016 | Shioda et al. |
| 2016/0159798 A1 | 6/2016 | Guzzo et al. |
| 2016/0237059 A1 | 8/2016 | Straub et al. |
| 2016/0257641 A1 | 9/2016 | Kobayashi et al. |
| 2016/0264567 A1 | 9/2016 | Yuen et al. |
| 2017/0204095 A1 | 7/2017 | Guzzo et al. |
| 2017/0267672 A1 | 9/2017 | Stoller et al. |

FOREIGN PATENT DOCUMENTS

| | | |
|---|---|---|
| JP | S59-104364 A | 6/1984 |
| JP | 2011-506491 A | 3/2011 |
| JP | 2013-515688 A | 5/2013 |
| WO | 1999-028301 A1 | 6/1999 |
| WO | 2009-089482 A1 | 7/2009 |
| WO | 2010-063663 A1 | 6/2010 |
| WO | 2013-004332 A1 | 1/2013 |
| WO | 2015-016372 A1 | 2/2015 |
| WO | 2015-036560 A1 | 3/2015 |
| WO | 2015-056782 A1 | 4/2015 |
| WO | 2016-030229 A1 | 3/2016 |
| WO | 2016-113205 A1 | 7/2016 |
| WO | 2016-128529 A1 | 8/2016 |

OTHER PUBLICATIONS

Inouye, Y, et al., "A Facile One-pot Preparation of 2-Methyl- and 2-Phenyl-4-fluoro-5-trifluoromethyl-6-methoxypyrimidine from Methyl 2-hydryl-2-(F-methyl)-F-propyl Ether", Journal of Fluorine Chemistry, 1985, 27 ( 2 ), pp. 231-236, DOI 10.1016/S0022-1139(00)84991-X, entire text (6 pages).

Zhang, Pei-Zhi, et al., "Direct regioselective Csp2-H trifluoromethylation of pyrimidinones and pyridinones", Tetrahedron, vol. 72, 2016, pp. 3250-3255 (6 pages).

Yang, Bin, et al., "Visible-Light Photoredox Decarboxylation of Perfluoroarene Iodine(III) Trifluoroacetates for C-H Trifluoromethylation of (Hetero)arenes", ACS Catalysis, vol. 8,, pp. 2839-2843, Published 2018 (5 pages).

Ouyang, Yao, et al., "Trifluoromethanesulfonic Anhydride as a Low-Cost and Versatile Trifluoromethylation Reagent", Angewandte Chem. Int. Ed 2018, vol. 57, pp. 6926-6929, 2018 (4 pages).

International Search Report (English and Japanese) and Written Opinion (in Japanese) of the International Searching Authority issued in PCT/JP2019/046489, mailed Feb. 10, 2020; ISA/JP (10 pages).

1st Chinese Office Action for corresponding Application No. CN 201980061589.7 dated Jul. 30, 2021 with English translation (15 pages).

European Search Report issued for the corresponding European Patent Application No. 19893651.0; dated Aug. 1, 2022 (total 6 pages).

FLUORINE-CONTAINING PYRIMIDINE COMPOUND AND METHOD FOR MANUFACTURING THE SAME

CROSS REFERENCE TO RELATED APPLICATIONS

The present application is a national stage application of International Patent Application No. PCT/JP2019/046489 filed on Nov. 28, 2019, which claims the benefit of Japanese Patent Application No. 2018-229889, filed on Dec. 7, 2018.

BACKGROUND

Technical Field

The present disclosure relates to a fluorine-containing pyrimidine compound and a method for manufacturing the same.

Description of the Related Art

Conventionally, it has been reported that fluorine-containing pyrimidine compounds have various biological activities. Among others, a compound having a pyridine ring structure or diazine ring structure at the 2-position of its pyrimidine ring is promising for use in pharmaceutical and agrochemical fields.

More specifically, a compound having a pyridine ring at the 2-position of its pyrimidine ring and having a trifluoromethyl group at the 5-position of its pyrimidine ring is disclosed in International Publication No. WO2009/089482, International Publication No. WO2015/056782, International Publication No. WO2015/016372, International Publication No. WO2010/063663, International Publication No. WO2013/004332, International Publication No. WO2016/030229, and International Publication No. WO1999/028301. International Publication No. WO2009/089482 and International Publication No. WO2015/056782 report that a 2-(4-pyridyl)-5-trifluoromethylpyrimidine derivative has a human melanin-concentrating hormone-inhibiting activity and an acetyl-CoA carboxylase 2-inhibiting activity. International Publication No. WO2015/056782, International Publication No. WO2015/016372, International Publication No. WO2010/063663, International Publication No. WO2013/004332 and International Publication No. WO2016/030229 report that a 2-(3-pyridyl)-5-trifluoromethylpyrimidine derivative has a disinfecting activity, an insecticidal activity, an orexin receptor-inhibiting activity, a focal adhesion kinase-inhibiting activity, and an acetyl-CoA carboxylase 2-inhibiting activity. International Publication No. WO2015/056782 and International Publication No. WO1999/028301 report that a 2-(2-pyridyl)-5-trifluoromethylpyrimidine derivative has a disinfecting activity, an insecticidal activity, and an herbicide activity. From such viewpoints, in expectation of further improvement in activities, introduction of substituents into the 4- and 6-positions of a pyrimidine ring receives interest.

In addition, a compound having a diazine ring structure at the 2-position of its pyrimidine ring is disclosed International Publication No. WO2015/016372, International Publication No. WO2016/113205, International Publication No. WO2016/128529 and International Publication No. WO2015/036560. International Publication No. WO2015/016372 discloses disinfecting and insecticidal activities of a compound having a 2-(2-pyrazyl)-pyrimidine structure or 2-(2-pyrimidyl)-pyrimidine structure, International Publication No. WO2016/113205 discloses a suppressing activity of a compound having a 2-(3-pyridazyl)-pyrimidine structure or 2-(2-pyrazyl)-pyrimidine structure against fibrotic diseases, International Publication No. WO2016/128529 discloses suppressing activities of a compound having a 2-(4-pyrimidyl)-pyrimidine structure or 2-(5-pyrimidyl)-pyrimidine structure against pain and asthma, and International Publication No. WO2015/036560 discloses suppressing activities of a compound having a 2-(4-pyridazyl)-pyrimidine structure against aching pain and asthma.

A synthesis method of a pyrimidine compound having a trifluoromethyl group at the 5-position and having substituents at the 4- and 6-positions of its pyrimidine ring is disclosed in Tetrahedron, 2016, 72, pp. 3250-3255, ACS Catalysis, 2018, 8, pp. 2839-2843, and Angewandte Chemie International Edition, 2018, 57, pp. 6926-6929. More specifically, Tetrahedron, 2016, 72, pp. 3250-3255 reports a synthesis method using sodium trifluoromethanesulfinate (Langlois reagent), ACS Catalysis, 2018, 8, pp. 2839-2843 reports a synthesis method using a trifluoroacetic acid derivative, and Angewandte Chemie International Edition, 2018, 57, pp. 6926-6929 reports a synthesis method using trifluoromethanesulfonic anhydride.

Technical Problem

However, manufacturing of a fluorine-containing pyrimidine compound having a fluorine-containing substituent at the 5-position, having a heterocyclic ring at the 2-position as a substituent, and having substituents at the 4- and 6-positions has been hitherto difficult in terms of reactivity and selectivity, and such a fluorine-containing pyrimidine compound has not been reported. The fluorine-containing pyrimidine compound is expected to have various biological activities, and a new fluorine-containing pyrimidine compound having substituents at the 4- and 6-positions and having a heterocyclic ring at the 2-position as a substituent and a manufacturing method thereof have been desired to be established.

Since regioselectivity at the time of introducing trifluoromethyl group is low in the manufacturing method reported in Tetrahedron, 2016, 72, pp. 3250-3255, introduction efficiency of trifluoromethyl group may decrease or introduction of trifluoromethyl group may become difficult with respect to a substrate having a plurality of heterocyclic rings such as a pyrimidine compound having a heterocyclic ring substituent. In addition, there has been a problem of not only using Langlois reagent as a trifluoromethylating agent in an amount of three times the amount of a substrate but also separately using manganese (III) acetate hydrate, which is toxic, as an oxidant in an amount of three times the amount of the substrate.

It is thought that a compound obtained by the manufacturing methods reported in ACS Catalysis, 2018, 8, pp. 2839-2843 and Angewandte Chemie International Edition, 2018, 57, pp. 6926-6929 is further modified and derivatized to be converted to the fluorine-containing pyrimidine compound. However, complication or a decrease in efficiency due to an increase in the number of processes cannot be sometimes avoided, or manufacturing of the fluorine-containing pyrimidine compound itself is sometimes difficult. In addition, these manufacturing methods are not considered to be suitable for practical use because a trifluoromethylating agent is required to be used in an amount of 2.5 to 3 times the amount of a substrate and light irradiation in the presence of a ruthenium complex catalyst is required.

Then, the present inventors have found that a pyridine ring structure or a diazine ring structure can be introduced into the 2-position between two nitrogen atoms on a pyrimidine ring by reacting specific raw materials and completed the present disclosure thereby. That is, the present disclosure provides a new fluorine-containing pyrimidine compound having substituents at the 4- and 6-position and having a pyridine ring structure or a diazine ring structure at the 2-position as a substituent and a manufacturing method capable of simply manufacturing the fluorine-containing pyrimidine compound, which are heretofore unknown.

SUMMARY

Purports and configurations of the present disclosure are as follows.

[1] A fluorine-containing pyrimidine compound represented by a general formula (1), (2), (3), (4), (5), or (6) below:

[Formula 1]

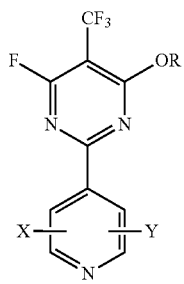

(1)

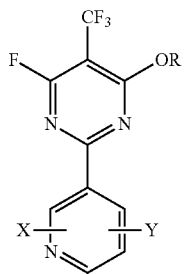

(2)

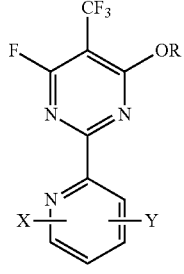

(3)

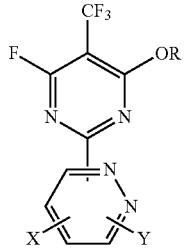

(4)

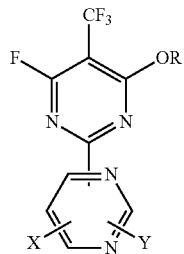

(5)

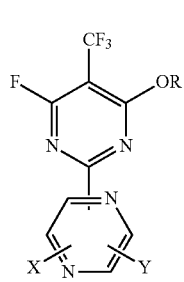

(6)

wherein, in the general formulae (1) to (6) above,

R represents a hydrocarbon group having 1 to 12 carbon atoms, and

X and Y each independently represent a hydrogen atom, a halogen atom, a hydrocarbon group having 1 to 10 carbon atoms, $-C_nF_{2n+1}$ (n is an integer of 1 to 10), a nitro group, a boronate group, $-OA^1$, $-SO_mA^1$ (m is an integer of 0 to 3), $-NA^1A^2$, $-COOA^1$, or $-CONA^1A^2$, and $A^1$ and $A^2$ each independently represent a hydrogen atom or a hydrocarbon group having 1 to 10 carbon atoms.

[2] The fluorine-containing pyrimidine compound according to [1] above, wherein the R is an alkyl group having 1 to 10 carbon atoms.

[3] A method for manufacturing a fluorine-containing pyrimidine compound, including:

(a) reacting a fluoroisobutylene derivative represented by a general formula (7) below with a compound represented by a general formula (8) below or a salt thereof to provide a fluorine-containing pyrimidine compound of a general formula (1) below,

[Formula 2]

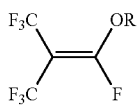

(7)

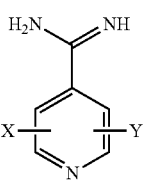

(8)

-continued

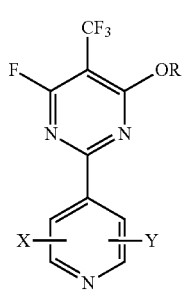
(1)

(b) reacting a fluoroisobutylene derivative represented by a general formula (7) below with a compound represented by a general formula (9) below or a salt thereof to provide a fluorine-containing pyrimidine compound of a general formula (2) below,

[Formula 3]

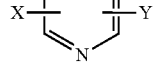
(7)

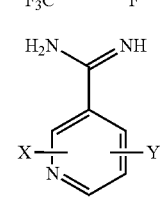
(9)

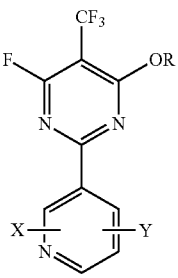
(2)

(c) reacting a fluoroisobutylene derivative represented by a general formula (7) below with a compound represented by a general formula (10) below or a salt thereof to provide a fluorine-containing pyrimidine compound of a general formula (3) below,

[Formula 4]

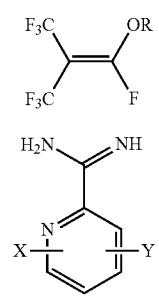
(7)

(10)

-continued

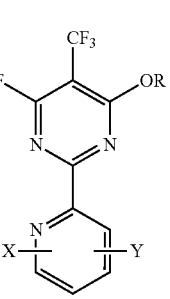
(3)

(d) reacting a fluoroisobutylene derivative represented by a general formula (7) below with a compound represented by a general formula (11) below or a salt thereof to provide a fluorine-containing pyrimidine compound of a general formula (4) below,

[Formula 5]

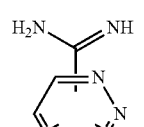
(7)

(11)

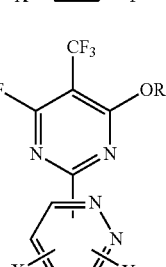
(4)

(e) reacting a fluoroisobutylene derivative represented by a general formula (7) below with a compound represented by a general formula (12) below or a salt thereof to provide a fluorine-containing pyrimidine compound of a general formula (5) below,

[Formula 6]

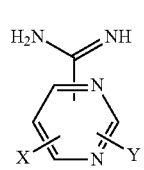
(7)

(12)

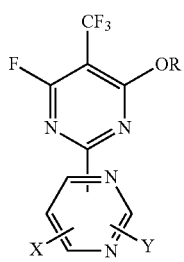
(5)

or (f) reacting a fluoroisobutylene derivative represented by a general formula (7) below with a compound represented by a general formula (13) below or a salt thereof to provide a fluorine-containing pyrimidine compound of a general formula (6) below,

[Formula 7]

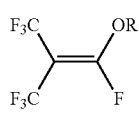
(7)

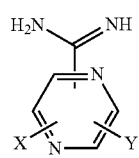
(13)

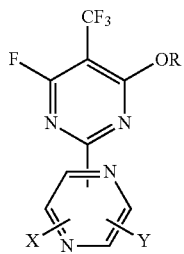
(6)

wherein, in the general formulae (1) to (13) above,

R represents a hydrocarbon group having 1 to 12 carbon atoms, and

X and Y each independently represent a hydrogen atom, a halogen atom, a hydrocarbon group having 1 to 10 carbon atoms, —$C_nF_{2n+1}$ (n is an integer of 1 to 10), a nitro group, a boronate group, —$OA^1$, —$SO_mA^1$ (m is an integer of 0 to 3), —$NA^1A^2$, —$COOA^1$, or —$CONA^1A^2$, and $A^1$ and $A^2$ each independently represent a hydrogen atom or a hydrocarbon group having 1 to 10 carbon atoms.

[4] A method for manufacturing a fluorine-containing pyrimidine compound, including:

(g) reacting a fluoroisobutane derivative represented by a general formula (14) below with a compound represented by a general formula (8) below or a salt thereof to provide a fluorine-containing pyrimidine compound of a general formula (1) below,

[Formula 8]

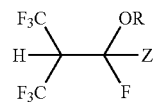
(14)

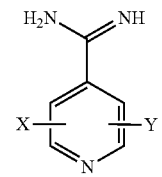
(8)

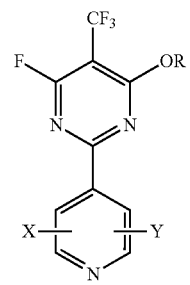
(1)

(h) reacting a fluoroisobutane derivative represented by a general formula (14) below with a compound represented by a general formula (9) below or a salt thereof to provide a fluorine-containing pyrimidine compound of a general formula (2) below,

[Formula 9]

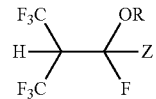
(14)

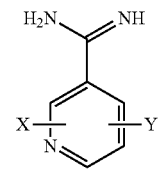
(9)

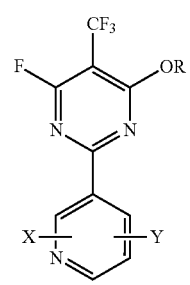
(2)

(i) reacting a fluoroisobutane derivative represented by a general formula (14) below with a compound represented by a general formula (10) below or a salt thereof to provide a fluorine-containing pyrimidine compound of a general formula (3) below,

[Formula 10]

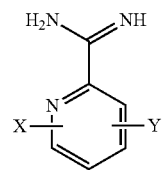
(14)

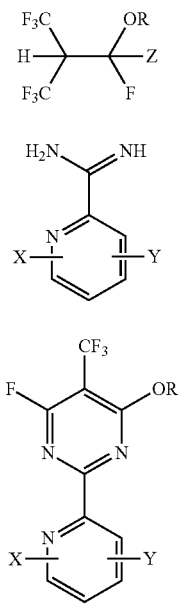
(10)

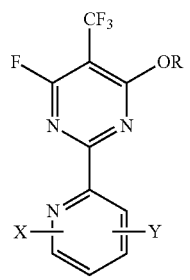
(3)

(j) reacting a fluoroisobutane derivative represented by a general formula (14) below with a compound represented by a general formula (11) below or a salt thereof to provide a fluorine-containing pyrimidine compound of a general formula (4) below,

[Formula 11]

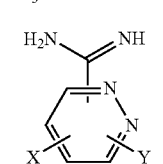
(14)

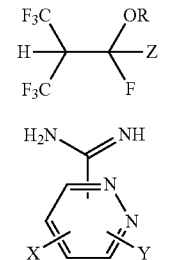
(11)

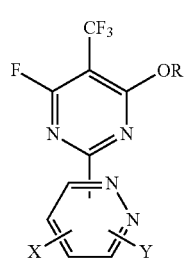
(4)

(k) reacting a fluoroisobutane derivative represented by a general formula (14) below with a compound represented by a general formula (12) below or a salt thereof to provide a fluorine-containing pyrimidine compound of a general formula (5) below,

[Formula 12]

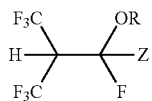
(14)

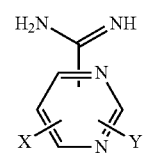
(12)

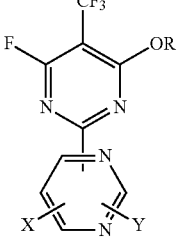
(5)

or (l) reacting a fluoroisobutane derivative represented by a general formula (14) below with a compound represented by a general formula (13) below or a salt thereof to provide a fluorine-containing pyrimidine compound of a general formula (6) below,

[Formula 13]

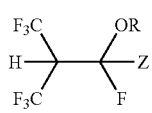
(14)

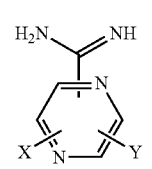
(13)

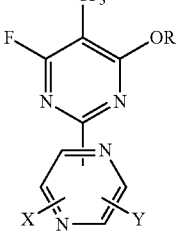
(6)

wherein, in the general formulae (1) to (6) and (8) to (14) above,

R represents a hydrocarbon group having 1 to 12 carbon atoms,

X and Y each independently represent a hydrogen atom, a halogen atom, a hydrocarbon group having 1 to 10 carbon atoms, $-C_nF_{2n+1}$ (n is an integer of 1 to 10), a nitro group, a boronate group, $-OA^1$, $-SO_mA^1$ (m is an integer of 0 to 3), $-NA^1A^2$, $-COOA^1$, or $-CONA^1A^2$, Z represents a halogen atom, $-OA^1$, $-SO_mA^1$ (m is an integer of 0 to 3), or $-NA^1A^2$, and A[1] and A[2] each independently represent a hydrogen atom or a hydrocarbon group having 1 to 10 carbon atoms.

[5] The method for manufacturing a fluorine-containing pyrimidine compound according to [3] above, wherein the R is an alkyl group having 1 to 10 carbon atoms.

[6] The method for manufacturing a fluorine-containing pyrimidine compound according to [4] above, wherein the R is an alkyl group having 1 to 10 carbon atoms.

Effects of Disclosure

A new fluorine-containing pyrimidine compound having substituents at the 4- and 6-position and having a pyridine ring structure or a diazine ring structure at the 2-position as a substituent and a manufacturing method capable of simply manufacturing the fluorine-containing pyrimidine compound can be provided.

DETAILED DESCRIPTION (Fluorine-Containing Pyrimidine Compound)

A fluorine-containing pyrimidine compound according to one embodiment is represented by general formula (1), (2), (3), (4), (5), or (6) below.

[Formula 14]

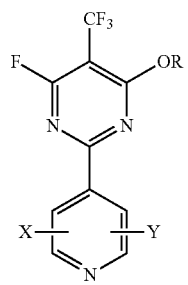

(1)

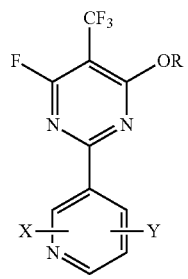

(2)

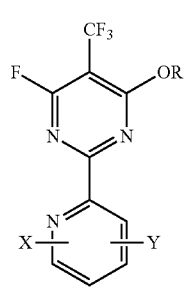

(3)

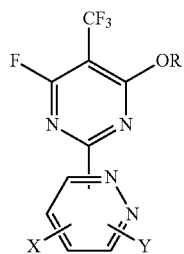

(4)

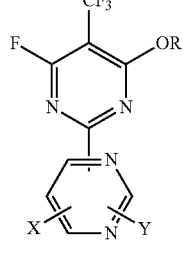

(5)

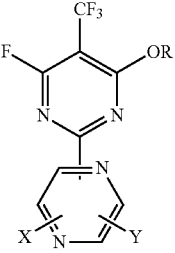

(6)

(In the general formulae (1) to (6) above,

R represents a hydrocarbon group having 1 to 12 carbon atoms, and

X and Y each independently represent a hydrogen atom, a halogen atom, a hydrocarbon group having 1 to 10 carbon atoms, $-C_nF_{2n+1}$ (n is an integer of 1 to 10), a nitro group, a boronate group, $-OA^1$, $-SO_mA^1$ (m is an integer of 0 to 3), $-NA^1A^2$, $-COOA^1$, or $-CONA^1A^2$, and $A^1$ and $A^2$ each independently represent a hydrogen atom or a hydrocarbon group having 1 to 10 carbon atoms.)

R is not particularly limited as long as R is a hydrocarbon group consisting of carbon atoms and hydrogen atoms, having 1 to 12 carbon atoms; and R can include a chain hydrocarbon group, an aromatic hydrocarbon group, an alicyclic hydrocarbon group, and the like. The chain hydrocarbon group is not particularly limited as long as it has 1 to 12 carbon atoms in total and may be a branched chain hydrocarbon group or may be a non-branched chain hydrocarbon group. The aromatic hydrocarbon group is not particularly limited as long as it has 6 to 12 carbon atoms in total and may be an aromatic hydrocarbon group having a substituent or may be an aromatic hydrocarbon group having no substituent. In addition, the aromatic hydrocarbon group may have a condensed polycyclic structure. The alicyclic hydrocarbon group is not particularly limited as long as it has 3 to 12 carbon atoms in total and may be an alicyclic hydrocarbon group having a substituent or may be an alicyclic hydrocarbon group having no substituent. In addition, the alicyclic hydrocarbon group may have a bridged cyclic structure.

The chain hydrocarbon group can include an alkyl group such as methyl group, ethyl group, n-propyl group, i-propyl group, n-butyl group, i-butyl group, sec-butyl group, t-butyl group, pentyl group, hexyl group, heptyl group, octyl group, nonyl group, decyl group, undecyl group, and dodecyl group;

an alkenyl group such as ethenyl group, propenyl group, butenyl group, pentenyl group, hexenyl group, heptenyl group, octenyl group, nonenyl group, decenyl group, undecenyl group, and dodecenyl group;

an alkynyl group such as ethynyl group, propynyl group, butynyl group, pentynyl group, hexynyl group, heptynyl group, octynyl group, nonynyl group, decynyl group, undecynyl group, and dodecynyl group; and the like.

The aromatic hydrocarbon group can include phenyl group and naphthyl group.

The alicyclic hydrocarbon group includes a saturated or unsaturated cyclic hydrocarbon group, and examples of the cyclic hydrocarbon group can include a cyclopropyl group, cyclobutyl group, cyclohexyl group, cyclopentyl group, adamantyl group, norbornyl group, and the like.

Preferably, R is an alkyl group having 1 to 10 carbon atoms. When R is an alkyl group having 1 to 10 carbon atoms, the fluoroisobutylene derivative of general formula (7) and the fluoroisobutane derivative of general formula (14), which are raw materials of the fluorine-containing pyrimidine compound, can be easily prepared.

$A^1$ included in $—OA^1$ and $—SO_mA^1$ (m is an integer of 0 to 3) represented as X or Y represents a hydrogen atom or a hydrocarbon group having 1 to 10 carbon atoms. $A^1$ and $A^2$ included in $—NA^1A^2$ represented as X or Y each independently represent a hydrogen atom or a hydrocarbon group having 1 to 10 carbon atoms. In a case where $A^1$ and $A^2$ represent a hydrocarbon group having 1 to 10 carbon atoms, $A^1$ and $A^2$ may be the hydrocarbon group having 1 to 10 carbon atoms of R described above, for example.

$A^1$ included in $—COOA^1$ represented as X or Y is a hydrogen atom or a hydrocarbon group having 1 to 10 carbon atoms and may be the hydrocarbon group having 1 to 10 carbon atoms of R described above, for example.

$A^1$ and $A^2$ included in $—CONA^1A^2$ represented as X or Y each independently represent a hydrogen atom or a hydrocarbon group having 1 to 10 carbon atoms. In a case where $A^1$ and $A^2$ represent a hydrocarbon group having 1 to 10 carbon atoms, $A^1$ and $A^2$ may be the hydrocarbon group having 1 to 10 carbon atoms of R described above, for example.

It is preferable that X and Y are each independently a hydrogen atom, a halogen atom (fluorine atom, chlorine atom, bromine atom, or iodine atom), a nitro group, a methyl group, an ethyl group, an n-propyl group, a methoxy group, an ethoxy group, a propoxy group, a dimethylamino group, a diethylamino group, a methylethylamino group, a methylsulfanyl group, an ethylsulfanyl group, a methoxycarbonyl group, an ethoxycarbonyl group, or a trifluoromethyl group, and it is more preferable that X and Y are each independently a hydrogen atom, a halogen atom (fluorine atom, chlorine atom, bromine atom, or iodine atom), a nitro group, a methyl group, an n-propyl group, a methoxy group, a dimethylamino group, a methylsulfanyl group, a methoxycarbonyl group, or a trifluoromethyl group. In addition, it is further preferable that the substituent bonded to the 2-position of the pyrimidine ring is 4-pyridyl group, 3-pyridyl group, 2-pyridyl group, 2,6-dichloro-4-pyridyl group, 4-nitro-2-pyridyl group, 3-methyl-2-pyridyl group, 3-fluoro-2-pyridyl group, 6-bromo-3-pyridyl group, 6-methoxy-3-pyridyl group, 2-dimethylamino-4-pyridyl group, 4-methylsulfanyl-2-pyridyl group, 4-methoxycarbonyl-2-pyridyl group, 2-pyrazyl group, 2-pyrimidyl group, 6-trifluoromethyl-3-pyridyl group, 6-n-propyl-2-pyridyl group, 3-pyridazinyl group, 4-pyrimidyl group, 4-pyridazinyl group, 5-pyrimidyl group, 6-chloro-3-pyridazinyl group, 5-chloro-3-pyrazyl group, 5-fluoro-2-pyrimidyl group, 5-bromo-2-pyrimidyl group, 4-methyl-2-pyrimidyl group, 5-methyl-4-pyridazinyl group, 4-trifluoromethyl-5-pyrimidyl group, 2-methylsulfanyl-5-pyrimidyl group, 2-dimethylamino-5-pyrimidyl group, or 6-methoxy-4-pyrimidyl group.

It is further preferable that the fluorine-containing pyrimidine compound is 6-fluoro-4-methoxy-2-(4-pyridyl)-5-trifluoromethylpyrimidine, 6-fluoro-4-methoxy-2-(3-pyridyl)-5-trifluoromethylpyrimidine, 6-fluoro-4-methoxy-2-(2-pyridyl)-5-trifluoromethylpyrimidine, 6-fluoro-4-methoxy-2-(2,6-dichloro-4-pyridyl)-5-trifluoromethylpyrimidine, 6-fluoro-4-methoxy-2-(4-nitro-2-pyridyl)-5-trifluoromethylpyrimidine, 6-fluoro-4-methoxy-2-(3-methyl-2-pyridyl)-5-trifluoromethylpyrimidine, 6-fluoro-4-methoxy-2-(3-fluoro-2-pyridyl)-5-trifluoromethylpyrimidine, 6-fluoro-4-methoxy-2-(6-bromo-3-pyridyl)-5-trifluoromethylpyrimidine, 6-fluoro-4-methoxy-2-(6-methoxy-3-pyridyl)-5-trifluoromethylpyrimidine, 6-fluoro-4-methoxy-2-(2-dimethylamino-4-pyridyl)-5-trifluoromethylpyrimidine, 6-fluoro-4-methoxy-2-(4-methylsulfanyl-2-pyridyl)-5-trifluoromethylpyrimidine, 6-fluoro-4-methoxy-2-(4-methoxycarbonyl-2-pyridyl)-5-trifluoromethylpyrimidine, 6-fluoro-4-methoxy-2-(2-pyrazyl)-5-trifluoromethylpyrimidine, 6-fluoro-4-methoxy-2-(2-pyrimidyl)-5-trifluoromethylpyrimidine, 6-fluoro-4-methoxy-2-(6-trifluoromethyl-3-pyridyl)-5-trifluoromethylpyrimidine, 6-fluoro-4-methoxy-2-(6-n-propyl-2-pyridyl)-5-trifluoromethylpyrimidine, 6-fluoro-4-methoxy-2-(3-pyridazinyl)-5-trifluoromethylpyrimidine, 6-fluoro-4-methoxy-2-(4-pyrimidyl)-5-trifluoromethylpyrimidine, 6-fluoro-4-methoxy-2-(4-pyridazinyl)-5-trifluoromethylpyrimidine, 6-fluoro-4-methoxy-2-(5-pyrimidyl)-5-trifluoromethylpyrimidine, 6-fluoro-4-methoxy-2-(6-chloro-3-pyridazinyl)-5-trifluoromethylpyrimidine, 6-fluoro-4-methoxy-2-(5-chloro-3-pyrazyl)-5-trifluoromethylpyrimidine, 6-fluoro-4-methoxy-2-(5-fluoro-2-pyrimidyl)-5-trifluoromethylpyrimidine, 6-fluoro-4-methoxy-2-(5-bromo-2-pyrimidyl)-5-trifluoromethylpyrimidine, 6-fluoro-4-methoxy-2-(4-methyl-2-pyrimidyl)-5-trifluoromethylpyrimidine, 6-fluoro-4-methoxy-2-(5-methyl-4-pyridazinyl)-5-trifluoromethylpyrimidine, 6-fluoro-4-methoxy-2-(4-trifluoromethyl-5-pyrimidyl)-5-trifluoromethylpyrimidine, 6-fluoro-4-methoxy-2-(2-methylsulfanyl-5-pyrimidyl)-5-trifluoromethylpyrimidine, 6-fluoro-4-methoxy-2-(2-dimethylamino-5-pyrimidyl)-5-trifluoromethylpyrimidine, or 6-fluoro-4-methoxy-2-(6-methoxy-4-pyrimidyl)-5-trifluoromethylpyrimidine By virtue of having a specific substituent (pyridyl group, pyridazyl group, pyrazyl group, or pyrimidyl group) on the 2-position of its pyrimidine ring and having specific substituents ($—OR$, $—CF_3$, and $—F$) on the 4-position, 5-position, and 6-position of its pyrimidine ring, the fluorine-containing pyrimidine compound of one embodiment can have an excellent effect in terms of structural expandability. Especially, a desired biological activity (for example, an inhibiting activity of a hormone or an enzyme, disinfecting activity, insecticidal activity, or herbicide activity) can be expected. The pyridine ring structure or diazine ring structure positioned on the 2-position of the pyrimidine ring may further have a substituent or may have no substituent. When the pyridine ring structure or diazine ring structure has a substituent, an additional property can be imparted to the fluorine-containing pyrimidine compound of one embodiment thereby. In addition, since the substituent on the 4-position and the substituent on the 6-position of the pyrimidine ring are different groups (—OR and —F) from each other, derivatization to an asymmetric structure can be easily proceeded, and use as an intermediate is also expected. More specifically, —OR can be modified by reacting the fluorine-containing pyrimidine compound under an acidic condition to obtain a derivative. In addition, —F can be modified by reacting the fluorine-containing pyrimidine compound under a basic condition to obtain a derivative. A fluorine-containing pyrimidine compound of one embodiment is useful in a field of electronic material such as organic semiconductors and liquid crystals, for example.

(Method for Manufacturing Fluorine-Containing Pyrimidine Compound)

A method for manufacturing a fluorine-containing pyrimidine compound according to one embodiment has:

(a) reacting a fluoroisobutylene derivative represented by general formula (7) below with a compound represented by general formula (8) below or a salt thereof to provide a fluorine-containing pyrimidine compound of general formula (1) below,

[Formula 15]

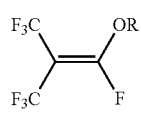
(7)

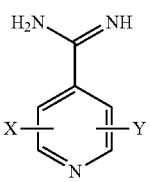
(8)

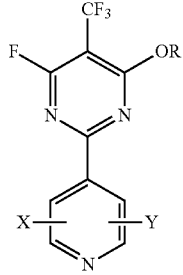
(1)

(b) reacting a fluoroisobutylene derivative represented by general formula (7) below with a compound represented by general formula (9) below or a salt thereof to provide a fluorine-containing pyrimidine compound of general formula (2) below,

[Formula 16]

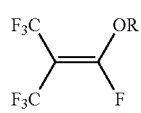
(7)

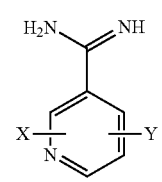
(9)

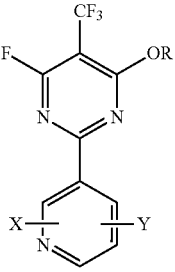
(2)

(c) reacting a fluoroisobutylene derivative represented by general formula (7) below with a compound represented by general formula (10) below or a salt thereof to provide a fluorine-containing pyrimidine compound of general formula (3) below,

[Formula 17]

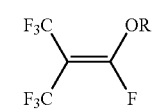
(7)

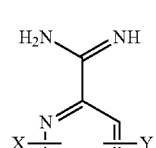
(10)

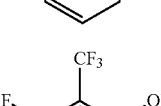
(3)

(d) reacting a fluoroisobutylene derivative represented by general formula (7) below with a compound represented by general formula (11) below or a salt thereof to provide a fluorine-containing pyrimidine compound of general formula (4) below,

[Formula 18]

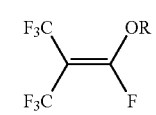
(7)

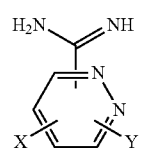
(11)

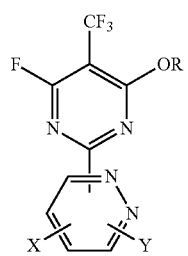
(4)

(e) reacting a fluoroisobutylene derivative represented by general formula (7) below with a compound represented by general formula (12) below or a salt thereof to provide a fluorine-containing pyrimidine compound of general formula (5) below,

[Formula 19]

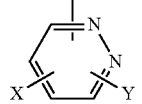
(7)

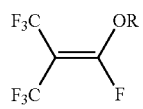
(12)

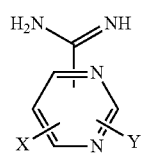
(5)

or (f) reacting a fluoroisobutylene derivative represented by general formula (7) below with a compound represented by general formula (13) below or a salt thereof to provide a fluorine-containing pyrimidine compound of general formula (6) below,

[Formula 20]

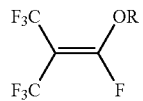
(7)

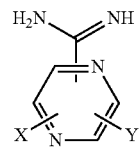
(13)

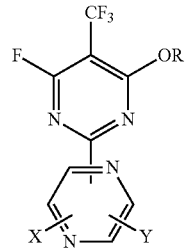
(6)

(in the general formulae (1) to (13) above,

R represents a hydrocarbon group having 1 to 12 carbon atoms,

X and Y each independently represent a hydrogen atom, a halogen atom, a hydrocarbon group having 1 to 10 carbon atoms, $-C_nF_{2n+1}$ (n is an integer of 1 to 10), a nitro group, a boronate group, $-OA^1$, $-SO_mA^1$ (m is an integer of 0 to 3), $-NA^1A^2$, $-COOA^1$, or $-CONA^1A^2$, and $A^1$ and $A^2$ each independently represent a hydrogen atom or a hydrocarbon group having 1 to 10 carbon atoms.). It is preferable that X and Y are each independently a hydrogen atom, a halogen atom (fluorine atom, chlorine atom, bromine atom, or iodine atom), a nitro group, a methyl group, an ethyl group, an n-propyl group, a methoxy group, an ethoxy group, a propoxy group, a dimethylamino group, a diethylamino group, a methylethylamino group, a methylsulfanyl group, an ethylsulfanyl group, a methoxycarbonyl group, an ethoxycarbonyl group, or a trifluoromethyl group, and it is more preferable that X and Y are each independently a hydrogen atom, a halogen atom (fluorine atom, chlorine atom, bromine atom, or iodine atom), a nitro group, a methyl group, an n-propyl group, a methoxy group, a dimethylamino group, a methylsulfanyl group, a methoxycarbonyl group, or a trifluoromethyl group. In addition, it is further preferable that the substituent bonded to the 2-position of the pyrimidine ring is 4-pyridyl group, 3-pyridyl group, 2-pyridyl group, 2,6-dichloro-4-pyridyl group, 4-nitro-2-pyridyl group, 3-methyl-2-pyridyl group, 3-fluoro-2-pyridyl group, 6-bromo-3-pyridyl group, 6-methoxy-3-pyridyl group, 2-dimethylamino-4-pyridyl group, 4-methylsulfanyl-2-pyridyl group, 4-methoxycarbonyl-2-pyridyl group, 2-pyrazyl group, 2-pyrimidyl group, 6-trifluoromethyl-3-pyridyl group, 6-n-propyl-2-pyridyl group, 3-pyridazinyl group, 4-pyrimidyl group, 4-pyridazinyl group, 5-pyrimidyl group, 6-chloro-3-pyridazinyl group, 5-chloro-3-pyrazyl group, 5-fluoro-2-pyrimidyl group, 5-bromo-2-pyrimidyl group, 4-methyl-2-pyrimidyl group, 5-methyl-4-pyridazinyl group, 4-trifluoromethyl-5-pyrimidyl group, 2-methylsulfanyl-5-pyrimidyl group, 2-dimethylamino-5-pyrimidyl group, or 6-methoxy-4-pyrimidyl group.

It is preferable that R in the general formulae (1) to (7) above represents an alkyl group having 1 to 10 carbon atoms.

The reaction between the fluoroisobutylene derivative represented by general formula (7) and the compound represented by general formula (8) in (a) above is represented by reaction formula (A) below.

[Formula 21]

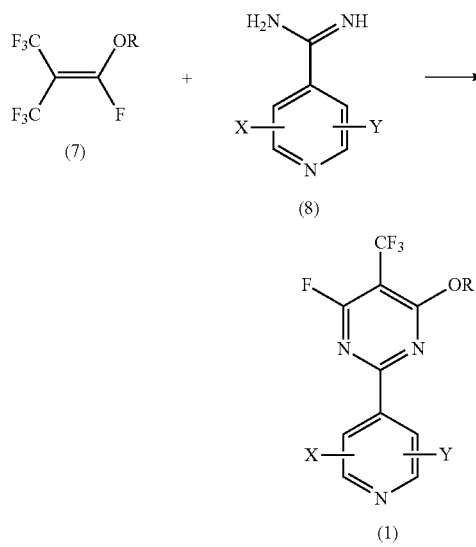

The reaction between the fluoroisobutylene derivative represented by general formula (7) and the compound represented by general formula (9) in (b) above is represented by reaction formula (B) below.

[Formula 22]

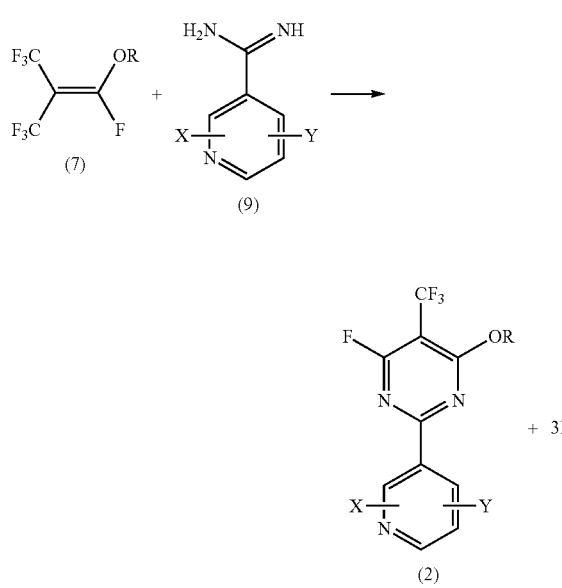

The reaction between the fluoroisobutylene derivative represented by general formula (7) and the compound represented by general formula (10) in (c) above is represented by reaction formula (C) below.

[Formula 23]

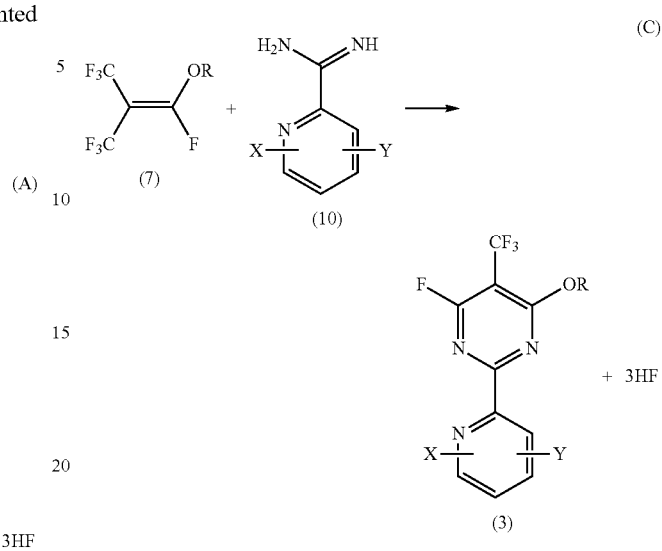

The reaction between the fluoroisobutylene derivative represented by general formula (7) and the compound represented by general formula (11) in (d) above is represented by reaction formula (D) below.

[Formula 24]

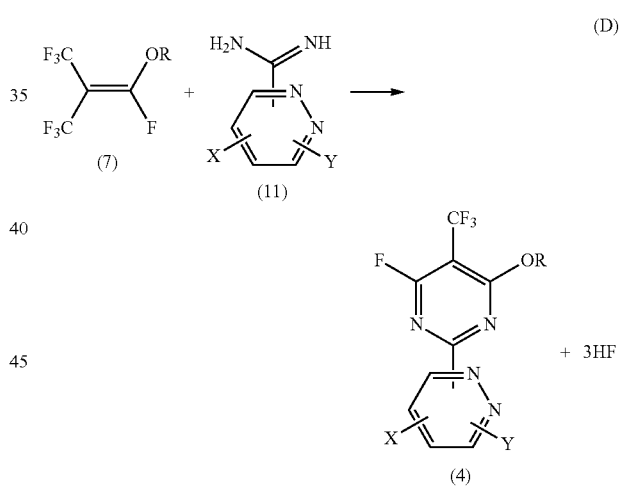

The reaction between the fluoroisobutylene derivative represented by general formula (7) and the compound represented by general formula (12) in (e) above is represented by reaction formula (E) below.

[Formula 25]

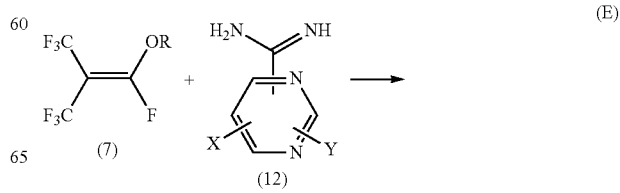

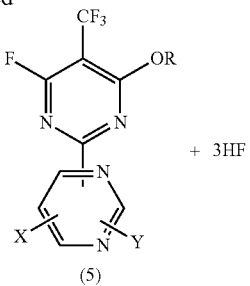

The reaction between the fluoroisobutylene derivative represented by general formula (7) and the compound represented by general formula (13) in (f) above is represented by reaction formula (F) below.

[Formula 26]

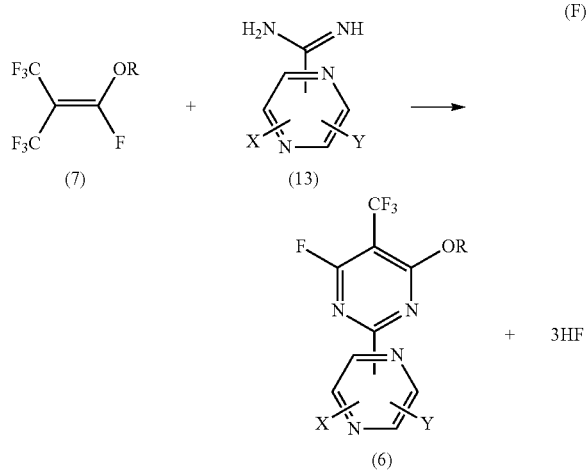

In reaction formulae (A) to (F) above, the compounds of general formulae (8) to (13) each may be a form of a salt. When the compound is in a form of a salt, a form in which at least one moiety of the amino moiety (—NH$_2$) and the imino moiety (=NH) forming the amidino group of each of the compounds of general formulae (8) to (13) is cationized to be (—NH$_3^+$) and (=NH$_2$+) to form a salt with a counter ion is exemplified. The counter ion is not particularly limited as long as it is a monovalent anion, and examples thereof can include halide ions such as F$^-$, Cl$^-$, Br$^-$, and I$^-$.

In the method for manufacturing a fluorine-containing pyrimidine compound according to one embodiment, the reactions of (a) to (f) above can be conducted in one step in the presence of a hydrogen halide-trapping agent, for example. Therefore, the fluorine-containing pyrimidine compounds of general formulae (1) to (6) above can be simply obtained. Incidentally, in the reactions of (a) to (f) above, a cyclic pyrimidine structure is formed between the fluoroisobutylene derivative and the amidino group of each of the compounds of general formulae (8) to (13). A group derived from the pyridine ring structure or diazine ring structure of each of the compounds of general formulae (8) to (13) is positioned at the 2-position of said pyrimidine structure. In addition, —OR, CF$_3$, and F derived from the fluoroisobutylene derivative are respectively positioned at the 4-position, 5-position, and 6-position of said pyrimidine structure.

The hydrogen halide-trapping agent is a substance having a function of trapping hydrogen fluoride (HF) formed from hydrogen atoms derived from the amidino group in each of the compounds of general formulae (8) to (13) and fluorine atoms derived from the fluoroisobutylene derivative of (7) in reaction formulae (A) to (F) above. As the hydrogen halide-trapping agent, sodium hydroxide, potassium hydroxide, calcium hydroxide, sodium carbonate, potassium carbonate, sodium fluoride, potassium fluoride, and an organic nitrogen derivative such as pyridine, triethylamine, diisopropylethylamine, diazabicyclononene, diazabicycloundecene, methyltriazabicyclodecene, and diazabicyclooctane can be used.

A reaction temperature during the reactions of (a) to (f) above is preferably 0 to 100° C., more preferably 5 to 50° C., and still more preferably 10 to 20° C. A reaction time for the reactions of (a) to (f) above is preferably 0.5 to 48 hours, more preferably 1 to 36 hours, and still more preferably 2 to 12 hours.

As a solvent used for the reactions of (a) to (f) above, an aprotic polar solvent such as tetrahydrofuran, monoglyme, diglyme, triglyme, tetraglyme, acetonitrile, dimethylformamide, dimethylacetamide, methylpyrrolidone, dimethylethyleneurea, tetramethylurea, dimethylsulfoxide, and sulfolan, or a two-phase system solvent of a protic polar solvent such as water and a water-insoluble solvent such as dichloromethane, toluene, and diethylether can be exemplified. In addition, as a catalyst for the reactions of (a) to (f) above, a quaternary ammonium halide such as benzyltriethylammonium chloride, a quaternary phosphonium halide, crown ethers, and the like can be used.

A method for manufacturing a fluorine-containing pyrimidine compound according to another embodiment has:

(g) reacting a fluoroisobutane derivative represented by general formula (14) below with a compound represented by general formula (8) below or a salt thereof to provide a fluorine-containing pyrimidine compound of general formula (1) below,

[Formula 27]

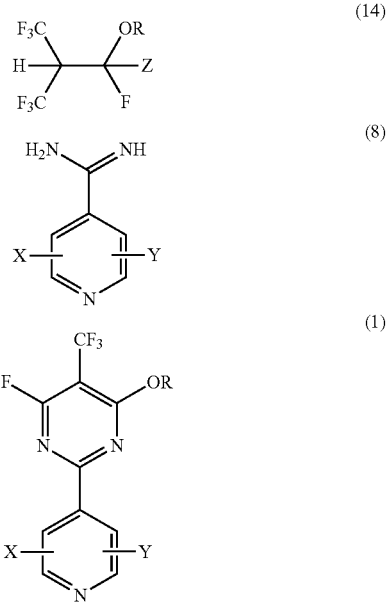

(h) reacting a fluoroisobutane derivative represented by general formula (14) below with a compound represented by general formula (9) below or a salt thereof to provide a fluorine-containing pyrimidine compound of general formula (2) below,

[Formula 28]

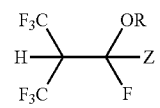
(14)

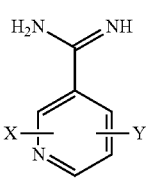
(9)

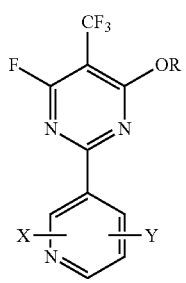
(2)

(i) reacting a fluoroisobutane derivative represented by general formula (14) below with a compound represented by general formula (10) below or a salt thereof to provide a fluorine-containing pyrimidine compound of general formula (3) below,

[Formula 29]

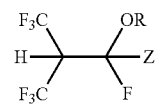
(14)

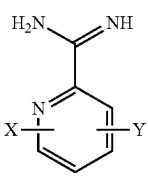
(10)

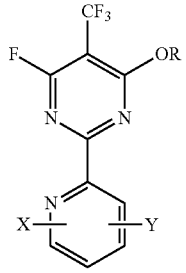
(3)

(j) reacting a fluoroisobutane derivative represented by general formula (14) below with a compound represented by general formula (11) below or a salt thereof to provide a fluorine-containing pyrimidine compound of general formula (4) below,

[Formula 30]

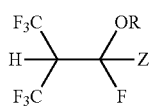
(14)

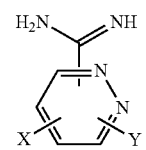
(11)

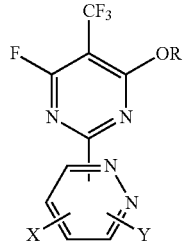
(4)

(k) reacting a fluoroisobutane derivative represented by general formula (14) below with a compound represented by general formula (12) below or a salt thereof to provide a fluorine-containing pyrimidine compound of general formula (5) below,

[Formula 31]

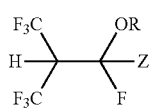
(14)

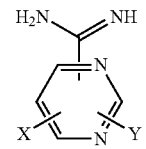
(12)

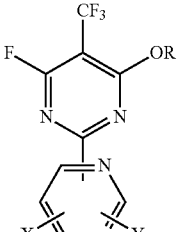
(5)

or (l) reacting a fluoroisobutane derivative represented by general formula (14) below with a compound represented by general formula (13) below or a salt thereof to provide a fluorine-containing pyrimidine compound of general formula (6) below,

[Formula 32]

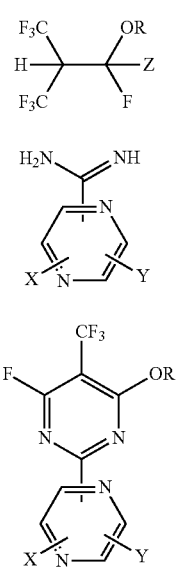

(in the formulae (1) to (6) and (8) to (14) above,

R represents a hydrocarbon group having 1 to 12 carbon atoms,

X and Y each independently represent a hydrogen atom, a halogen atom, a hydrocarbon group having 1 to 10 carbon atoms, —$C_nF_{2n+1}$ (n is an integer of 1 to 10), a nitro group, a boronate group, —$OA^1$, —$SO_mA^1$ (m is an integer of 0 to 3), —$NA^1A^2$, —$COOA^1$, or —$CONA^1A^2$, Z represents a halogen atom, —$OA^1$, —$SO_mA^1$ (m is an integer of 0 to 3), or —$NA^1A^2$, and $A^1$ and $A^2$ each independently represent a hydrogen atom or a hydrocarbon group having 1 to 10 carbon atoms.).

Specifically, $A^1$ and $A^2$ of the compounds of general formulae (1) to (6) and (8) to (14) in steps (g) to (l) above can be similar to $A^1$ and $A^2$ of the compounds of general formulae (1) to (7) in steps (a) to (f) above.

It is preferable that R of general formulae (1) to (6) and (14) above represents an alkyl group having 1 to 10 carbon atoms.

The reaction between the fluoroisobutane derivative represented by general formula (14) and the compound represented by general formula (8) in (g) above is represented by reaction formula (G) below.

[Formula 33]

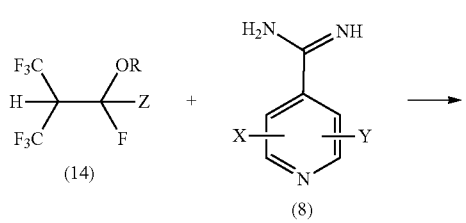

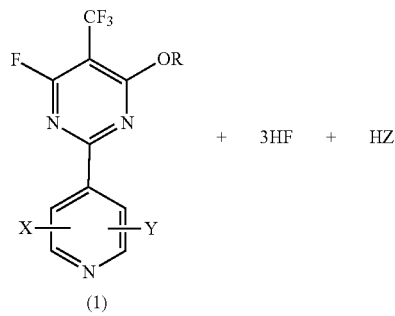

The reaction between the fluoroisobutane derivative represented by general formula (14) and the compound represented by general formula (9) in (h) above is represented by reaction formula (H) below.

[Formula 34]

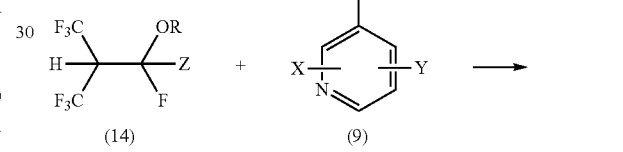

The reaction between the fluoroisobutane derivative represented by general formula (14) and the compound represented by general formula (10) in (i) above is represented by reaction formula (I) below.

[Formula 35]

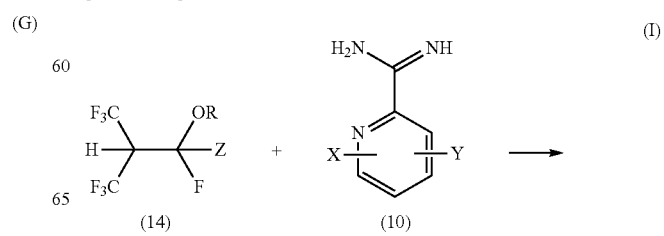

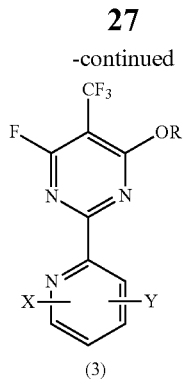

+ 3HF + HZ (3)

The reaction between the fluoroisobutane derivative represented by general formula (14) and the compound represented by general formula (11) in (j) above is represented by reaction formula (J) below.

[Formula 36]

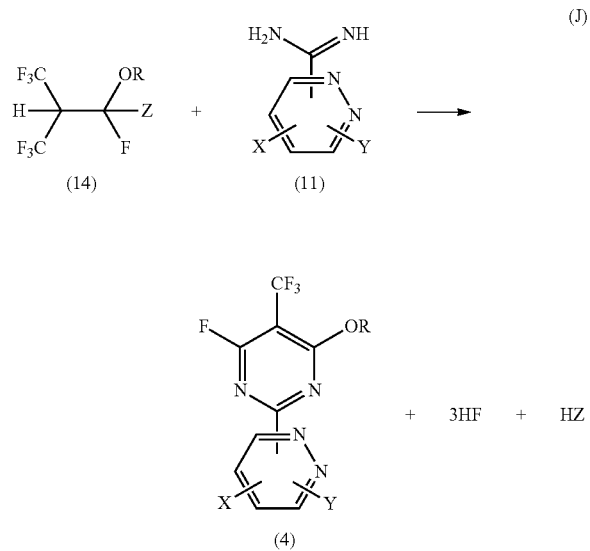

The reaction between the fluoroisobutane derivative represented by general formula (14) and the compound represented by general formula (12) in (k) above is represented by reaction formula (K) below.

[Formula 37]

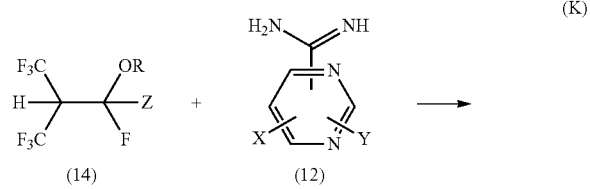

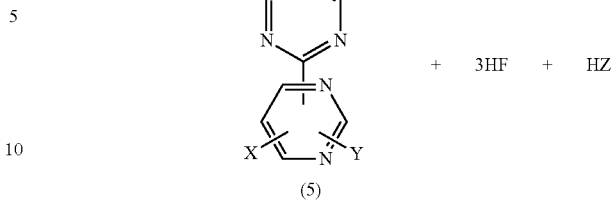

(5)

The reaction between the fluoroisobutane derivative represented by general formula (14) and the compound represented by general formula (13) in (l) above is represented by reaction formula (L) below.

[Formula 38]

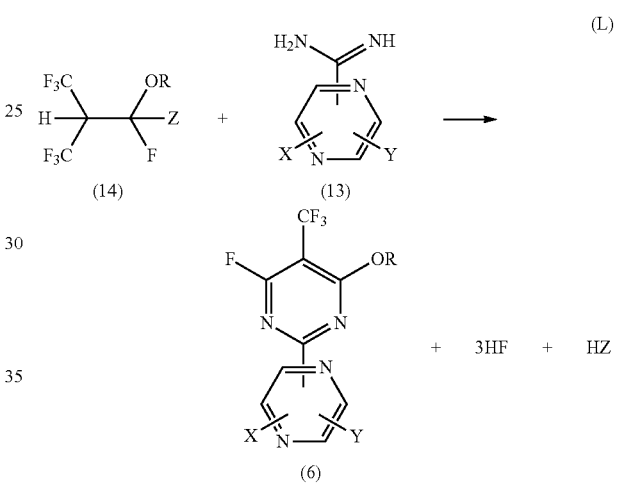

In reaction formulae (G) to (L) above, compounds of general formulae (8) to (13) each may be a form of a salt. When the compounds are in a form of a salt, a form in which at least one moiety of the amino moiety (—$NH_2$) and the imino moiety (=NH) forming the amidino group of each of the compounds of general formulae (8) to (13) is cationized to be (—$NH_3+$) and (=$NH_2+$) to form a salt with a counter ion is exemplified. The counter ion is not particularly limited as long as it is a monovalent anion, and examples thereof include halide ions such as $F^-$, $Cl^-$, $Br^-$, and $I^-$.

In the method for manufacturing a fluorine-containing pyrimidine compound according to said another embodiment, the reactions of (G) to (L) above can be conducted in one step, for example. Therefore, the fluorine-containing pyrimidine compounds of general formulae (1) to (6) above can be simply obtained. Incidentally, in the reactions of (g) to (l) above, a cyclic pyrimidine structure is formed between the fluoroisobutane derivative and the amidino group of each of the compounds of general formulae (8) to (13). A group derived from the pyridine ring structure or diazine ring structure of each of the compounds of general formulae (8) to (13) is positioned at the 2-position of said pyrimidine structure. In addition, —OR, $CF_3$, and F derived from the fluoroisobutane derivative are respectively positioned at the 4-position, 5-position, and 6-position of said pyrimidine structure.

A reaction temperature during the reactions of (g) to (l) above is preferably 0 to 100° C., more preferably 5 to 50° C., and still more preferably 10 to 20° C. A reaction time for the reactions of (g) to (l) above is preferably 0.5 to 48 hours, more preferably 1 to 36 hours, and still more preferably 4 to 24 hours. Hydrogen halide-trapping agents similar to those used in (a) to (f) above can be used in the reactions of (g) to (l) above.

As a solvent used for the reactions of (g) to (l) above, an aprotic polar solvent such as tetrahydrofuran, monoglyme, diglyme, triglyme, tetraglyme, acetonitrile, dimethylformamide, dimethylacetamide, methylpyrrolidone, dimethylethyleneurea, tetramethylurea, dimethylsulfoxide, and sulfolan, or a two-phase system solvent of a protic polar solvent such as water and a water-insoluble solvent such as dichloromethane, toluene, and diethylether can be exemplified. In addition, as a catalyst for the reactions of (g) to (l) above, a quaternary ammonium halide such as benzyltriethylammonium chloride, a quaternary phosphonium halide, crown ethers, and the like can be used.

Hereinabove, embodiments of the present disclosure have been described. However, the present disclosure is not limited to the above embodiments and includes various aspects encompassed by the concept and the scope of claims of the present disclosure, and various modifications can be made within the scope of the present disclosure.

EXAMPLES

Hereinafter, examples will be described in order to further clarify the effects of the present disclosure. However, the present disclosure is not limited to these examples.

Example 1

Manufacturing of 6-fluoro-4-methoxy-2-(4-pyridyl)-5-trifluoromethylpyrimidine

To 100 g of diethyl ether and 100 g of water were added 15 g (0.1 mol) of 4-amidinopyridine hydrochloride and 17 g (0.08 mol) of 1,3,3,3-tetrafluoro-1-methoxy-2-trifluoromethyl-1-propene under cooling with iced water. Subsequently, 63 ml (0.3 mol) of sodium hydroxide 5N aqueous solution (hydrogen halide-trapping agent) was dropped to the resultant mixture so that the internal temperature thereof did not exceed 10° C., and the resultant mixture was heated to room temperature. The resultant mixture was stirred for about 16 hours and subjected to extraction with hexane. The hexane phase was concentrated and subjected to column purification to provide 4.0 g (15 mmol) of the objective substance. A yield of the objective substance was 18%.

Analysis results of the obtained objective substance were as follows.

Mass spectrum (APCI, m/z): 274 ([M+H]$^+$)

$^1$H-NMR (300 MHz, CDCl$_3$) δ ppm: 8.83 (dd, 2H), 8.24 (dd, 2H), 4.27 (s, 3H)

$^{19}$F-NMR (300 MHz, C$_6$F$_6$) δ ppm: −58.80 (d, 3F), −60.69 (dd, 1F)

Example 2

Manufacturing of 6-fluoro-4-methoxy-2-(3-pyridyl)-5-trifluoromethylpyrimidine

To 100 g of acetonitrile were added 15 g (0.1 mol) of 3-amidinopyridine hydrochloride and 15 g (0.07 mol) of 1,3,3,3-tetrafluoro-1-methoxy-2-trifluoromethyl-1-propene under cooling with iced water. Subsequently, a mixed solution including 10 g (0.1 mol) of triethylamine (hydrogen halide-trapping agent) and 20 g of acetonitrile was dropped to the resultant mixture so that the internal temperature thereof did not exceed 10° C., and the resultant mixture was heated to room temperature. The resultant mixture was stirred for about 16 hours and subjected to extraction with hexane. The hexane phase was concentrated and subjected to column purification to provide 2.8 g (10 mmol) of the objective substance. A yield of the objective substance was 13%.

Analysis results of the obtained objective substance were as follows.

Mass spectrum (APCI, m/z): 274 ([M+H]$^+$)

$^1$H-NMR (300 MHz, CDCl$_3$) δ ppm: 9.63 (d, 1H), 8.80 (dd, 1H), 8.67 (ddd, 1H), 7.46 (dd, 1H), 4.27 (s, 3H)

$^{19}$F-NMR (300 MHz, C$_6$F$_6$) δ ppm: −58.63 (d, 3F), −60.91 (dd, 1F)

Example 3

Manufacturing of 6-fluoro-4-methoxy-2-(2-pyridyl)-5-trifluoromethylpyrimidine

To 100 g of acetonitrile were added 15 g (0.1 mol) of 3-amidinopyridine hydrochloride and 15 g (0.07 mol) of 1,3,3,3-tetrafluoro-1-methoxy-2-trifluoromethyl-1-propene under cooling with iced water. Subsequently, a mixed solution including 10 g (0.1 mol) of triethylamine (hydrogen halide-trapping agent) and 20 g of acetonitrile was dropped to the resultant mixture so that the internal temperature thereof did not exceed 10° C., and the resultant mixture was heated to room temperature. The resultant mixture was stirred for about 7 hours and subjected to extraction with hexane. The hexane phase was concentrated and subjected to column purification to provide 7.5 g (27 mmol) of the objective substance. A yield of the objective substance was 34%.

Analysis results of the obtained objective substance were as follows.

Mass spectrum (APCI, m/z): 274 ([M+H]$^+$)

$^1$H-NMR (300 MHz, CDCl$_3$) δ ppm: 8.87 (d, 1H), 8.50 (dd, 1H), 7.91 (ddd, 1H), 7.49 (ddd, 1H), 4.29 (s, 3H)

$^{19}$F-NMR (300 MHz, C$_6$F$_6$) δ ppm: −58.70 (d, 3F), −59.74 (dd, 1F)

Example 4

Manufacturing of 6-fluoro-4-methoxy-2-(4-pyridyl)-5-trifluoromethylpyrimidine using 1,1,1,3,3-pentafluoro-3-methoxy-2-trifluoromethyl-propane instead of 1,3,3,3-tetrafluoro-1-methoxy-2-trifluoromethyl-1-propene of Example 1

To 25 g of dichloromethane and 25 g of water were added 25 g (0.16 mol) of 4-amidinopyridinium hydrochloride and 28 g (0.12 mol) of 1,1,1,3,3-pentafluoro-3-methoxy-2-trifluoromethyl-propane under cooling with iced water to obtain a solution. Subsequently, 120 ml (0.6 mol) of sodium hydroxide 5N aqueous solution (hydrogen halide-trapping agent) was dropped to the solution so that the internal temperature thereof did not exceed 10° C. The solution was heated to room temperature after the dropping of the sodium hydroxide aqueous solution was completed. The solution was stirred for 3 hours and subsequently allowed to stand still, and the lower phase was slowly poured into 500 ml of HCl 1N aqueous solution. The lower phase thus obtained was dried with anhydrous sodium sulfate and filtered, and the obtained product was analyzed by GC-MS. As a result, a spectrum having a peak at the position corresponding to the molecular weight of 6-fluoro-4-methoxy-2-(4-pyridyl)-5-trifluoromethylpyrimidine was observed.

Analysis results of the obtained product were similar to those of the product in Example 1.

Example 5

Manufacturing of 6-fluoro-4-methoxy-2-(3-pyridyl)-5-trifluoromethylpyrimidine using 1,1,1,3,3-pentafluoro-3-methoxy-2-trifluoromethyl-propane instead of 1,3,3,3-tetrafluoro-1-methoxy-2-trifluoromethyl-1-propene of Example 2

To 25 g of dichloromethane and 25 g of water were added 25 g (0.16 mol) of 3-amidinopyridinium hydrochloride and 28 g (0.12 mol) of 1,1,1,3,3-pentafluoro-3-methoxy-2-trifluoromethyl-propane under cooling with iced water to obtain a solution. Subsequently, 120 ml (0.6 mol) of sodium hydroxide 5N aqueous solution (hydrogen halide-trapping agent) was dropped to the solution so that the internal temperature thereof did not exceed 10° C. The solution was heated to room temperature after the dropping of the sodium hydroxide aqueous solution was completed. The solution was stirred for 3 hours and subsequently allowed to stand still, and the lower phase of the solution was slowly poured into 500 ml of HCl 1N aqueous solution. The lower phase thus obtained was dried with anhydrous sodium sulfate and filtered, and the obtained product was analyzed by GC-MS. As a result, a spectrum having a peak at the position corresponding to the molecular weight of 6-fluoro-4-methoxy-2-(3-pyridyl)-5-trifluoromethylpyrimidine was observed.

Analysis results of the obtained product were similar to those of the product in Example 2.

Example 6

Manufacturing of 6-fluoro-4-methoxy-2-(2-pyridyl)-5-trifluoromethylpyrimidine using 1,1,1,3,3-pentafluoro-3-methoxy-2-trifluoromethyl-propane instead of 1,3,3,3-tetrafluoro-1-methoxy-2-trifluoromethyl-1-propene of Example 3

To 25 g of dichloromethane and 25 g of water were added 25 g (0.16 mol) of 2-amidinopyridinium hydrochloride and 28 g (0.12 mol) of 1,1,1,3,3-pentafluoro-3-methoxy-2-trifluoromethyl-propane under cooling with iced water to obtain a solution. Subsequently, 120 ml (0.6 mol) of sodium hydroxide 5N aqueous solution (hydrogen halide-trapping agent) was dropped to the solution so that the internal temperature thereof did not exceed 10° C. The solution was heated to room temperature after the dropping of the sodium hydroxide aqueous solution was completed. The solution was stirred for 3 hours and subsequently allowed to stand still, and the lower phase of the solution was slowly poured into 500 ml of HCl 1N aqueous solution. The lower phase thus obtained was dried with anhydrous sodium sulfate and filtered, and the obtained product was analyzed by GC-MS. As a result, a spectrum having a peak at the position corresponding to the molecular weight of 6-fluoro-4-methoxy-2-(2-pyridyl)-5-trifluoromethylpyrimidine was observed.

Analysis results of the obtained product were similar to those of the product in Example 3.

Example 7

Manufacturing of 6-fluoro-4-methoxy-2-(2,6-dichloro-4-pyridyl)-5-trifluoromethylpyrimidine To 2.2 ml of diethyl ether and 2.2 ml of water were added 0.5 g (2.2 mmol) of 2,6-chloropyridine-4-carboximidamide hydrochloride and 0.3 g (1.4 mmol) of 1,3,3,3-tetrafluoro-1-methoxy-2-trifluoromethyl-1-propene. Subsequently, 0.3 g (1.5 mmol) of sodium hydroxide 5N aqueous solution was added to the resultant mixture, and the resultant mixture was stirred for 15 hours. Subsequently, 1.1 g (5.5 mmol) of sodium hydroxide 5N aqueous solution (hydrogen halide-trapping agent) was added to the resultant mixture, and the resultant mixture was stirred at room temperature for 31 hours. After adding hexane and water, the resultant mixture was subjected to extraction with diethyl ether, and the organic phase was dried with sodium sulfate. The dried organic phase was subsequently concentrated and subjected to column purification to provide 0.3 g (0.7 mmol) of the objective substance with a yield of 51.7%. Analysis results of the obtained objective substance are as follows.

$^1$H NMR (400 MHz, CDCl$_3$) δ ppm: 8.20 (s, 2H), 4.28 (s, 3H). APCIMS m/z=342.3

Example 8

Manufacturing of 6-fluoro-4-methoxy-2-(4-nitro-2-pyridyl)-5-trifluoromethylpyrimidine To 1.5 ml of diethyl ether and 1.5 ml of water were added 0.3 g (1.4 mmol) of 4-nitropicolinimidamide hydrochloride and 0.4 g (1.9 mmol) of 1,3,3,3-tetrafluoro-1-methoxy-2-trifluoromethyl-1-propene. Subsequently, 1.7 g (8.5 mmol) of sodium hydroxide 5N aqueous solution (hydrogen halide-trapping agent) was added to the resultant mixture, and the resultant mixture was stirred for 16 hours. After adding water, the resultant mixture was subjected to extraction with diethyl ether, and the organic phase was dried with sodium sulfate. The dried organic phase was subsequently concentrated and subjected to column purification to provide 0.02 g (0.07 mmol) of the objective substance with a yield of 5.2%. Analysis results of the obtained objective substance are as follows.

$^1$H NMR (400 MHz, CDCl$_3$) δ ppm: 9.18 (d, J=5.2 Hz, 1H), 9.15 (d, J=2.0 Hz, 1H), 8.22 (dd, J=5.2, 2.4 Hz, 1H), 4.34 (s, 3H). APCIMS m/z=319.6

Example 9

Manufacturing of 6-fluoro-4-methoxy-2-(3-methyl-2-pyridyl)-5-trifluoromethylpyrimidine To 1.6 ml of diethyl ether and 1.6 ml of water were added 0.3 g (1.5 mmol) of 3-methylpyridine-2-carboximidamide hydrochloride and 0.4 g (1.9 mmol) of 1,3,3,3-tetrafluoro-1-methoxy-2-trifluoromethyl-1-propene. Subsequently, 1.6 g (8.0 mmol) of sodium hydroxide 5N aqueous solution (hydrogen halide-trapping agent) was added to the resultant mixture, and the resultant mixture was stirred for 16.5 hours. After adding water, the resultant mixture was subjected to extraction with diethyl ether, and the organic phase was dried with sodium sulfate. The dried organic phase was subsequently concentrated and subjected to column purification to provide 0.02 g (0.08 mmol) of the objective substance with a yield of 5.3%. Analysis results of the obtained objective substance are as follows.

$^1$H NMR (400 MHz, CDCl$_3$) δ ppm: 8.65 (d, J=4.8 Hz, 1H), 7.68 (d, J=8.0 Hz, 1H), 7.36 (dd, J=8.0, 4.8 Hz, 1H), 4.21 (s, 3H), 2.62 (s, 3H). APCIMS m/z=288.7

Example 10

Manufacturing of 6-fluoro-4-methoxy-2-(3-fluoro-2-pyridyl)-5-trifluoromethylpyrimidine To 2.0 ml of diethyl ether and 2.0 ml of water were added 0.4 g (2.0 mmol) of 3-fluoropicolinimidamide hydrochloride and 0.3 g (1.4 mmol) of 1,3,3,3-tetrafluoro-1-methoxy-2-trifluoromethyl-1-propene. Subsequently, 1.3 g (6.5 mmol) of sodium hydroxide 5N aqueous solution (hydrogen halide-trapping agent) was added to the resultant mixture, and the resultant mixture was stirred for one day. After adding water, the resultant mixture was subjected to extraction with diethyl ether, and the organic phase was dried with sodium sulfate. The dried organic phase was subsequently concentrated and subjected to column purification to provide 0.05 g (0.15 mmol) of the objective substance with a yield of 7.6%. Analysis results of the obtained objective substance are as follows.

$^1$H NMR (400 MHz, CDCl$_3$) δ ppm: 8.15 (m, 1H), 7.62 (m, 1H), 7.53 (dd, J=4.0, 8.4 Hz, 1H), 4.24 (s, 3H). APCIMS m/z=292.5

Example 11

Manufacturing of 6-fluoro-4-methoxy-2-(6-bromo-3-pyridyl)-5-trifluoromethylpyrimidine To 2.4 ml of diethyl ether and 2.4 ml of water were added 0.6 g (2.4 mmol) of 6-bromonicotinimidamide hydrochloride and 0.4 g (1.9 mmol) of 1,3,3,3-tetrafluoro-1-methoxy-2-trifluoromethyl-1-propene. Subsequently, 1.7 g (8.5 mmol) of sodium hydroxide 5N aqueous solution (hydrogen halide-trapping agent) was added to the resultant mixture, and the resultant mixture was stirred for 19.5 hours. After adding water, the resultant mixture was subjected to extraction with diethyl ether, and the organic phase was dried with sodium sulfate. The dried organic phase was subsequently concentrated and subjected to column purification to provide 0.27 g (0.78 mmol) of the objective substance with a yield of 31.0%. Analysis results of the obtained objective substance are as follows.

$^1$H NMR (400 MHz, CDCl$_3$) δ ppm: 9.35 (dd, J=0.8, 2.4 Hz, 1H), 8.50 (dd, J=2.4, 8.4 Hz, 1H), 7.64 (dd, J=0.8, 8.4 Hz, 1H), 4.25 (s, 3H). APCIMS m/z=352.7

Example 12

Manufacturing of 6-fluoro-4-methoxy-2-(6-methoxy-3-pyridyl)-5-trifluoromethylpyrimidine To 1.8 ml of diethyl ether and 1.8 ml of water were added 0.3 g (1.8 mmol) of 6-methoxynicotinimidamide hydrochloride and 0.6 g (2.8 mmol) of 1,3,3,3-tetrafluoro-1-methoxy-2-trifluoromethyl-1-propene. Subsequently, 1.2 g (6.0 mmol) of sodium hydroxide 5N aqueous solution (hydrogen halide-trapping agent) was added to the resultant mixture, and the resultant mixture was stirred for 18 hours. After adding water, the resultant mixture was subjected to extraction with diethyl ether, and the organic phase was dried with sodium sulfate. The dried organic phase was subsequently concentrated and subjected to column purification to provide 0.11 g (0.38 mmol) of the objective substance with a yield of 20.3%. Analysis results of the obtained objective substance are as follows.

$^1$H NMR (400 MHz, CDCl$_3$) δ ppm: 9.25 (dd, J=0.8, 2.4 Hz, 1H), 8.52 (dd, J=2.4, 8.8 Hz, 1H), 6.84 (dd, J=0.8, 8.8 Hz, 1H), 4.22 (s, 3H), 4.04 (s, 3H). APCIMS m/z=304.6

Example 13

Manufacturing of 6-fluoro-4-methoxy-2-(2-dimethylamino-4-pyridyl)-5-trifluoromethylpyrimidine To 2.0 ml of diethyl ether and 2.0 ml of water were added 0.4 g (2.0 mmol) of 2-(dimethylamino)pyridine-4-carboximidamide hydrochloride and 0.7 g (3.3 mmol) of 1,3,3,3-tetrafluoro-1-methoxy-2-trifluoromethyl-1-propene. Subsequently, 1.3 g (6.5 mmol) of sodium hydroxide 5N aqueous solution (hydrogen halide-trapping agent) was added to the resultant mixture, and the resultant mixture was stirred for 18 hours. After adding water, the resultant mixture was subjected to extraction with diethyl ether, and the organic phase was dried with sodium sulfate. The dried organic phase was subsequently concentrated and subjected to column purification to provide 0.11 g (0.34 mmol) of the objective substance with a yield of 18.8%. Analysis results of the obtained objective substance are as follows.

$^1$H NMR (400 MHz, CDCl$_3$) δ ppm: 8.33 (dd, J=0.4, 5.2 Hz, 1H), 7.50 (dd, J=0.8, 0.8 Hz, 1H), 7.64 (dd, J=1.2, 5.2 Hz, 1H), 4.25 (s, 3H), 3.19 (s, 6H). APCIMS m/z=317.9

Example 14

Manufacturing of 6-fluoro-4-methoxy-2-(4-methylsulfanyl-2-pyridyl)-5-trifluoromethylpyrimidine To 1.8 ml of diethyl ether and 1.8 ml of water were added 0.4 g (1.8 mmol) of 4-(methylsulfanyl)pyridine-2-carboximidamide hydrochloride and 0.3 g (1.4 mmol) of 1,3,3,3-tetrafluoro-1-methoxy-2-trifluoromethyl-1-propene. Subsequently, 1.3 g (6.5 mmol) of sodium hydroxide 5N aqueous solution (hydrogen halide-trapping agent) was added to the resultant mixture, and the resultant mixture was stirred for 18 hours. After adding water, the resultant mixture was subjected to extraction with diethyl ether, and the organic phase was dried with sodium sulfate. The dried organic phase was subsequently concentrated and subjected to column purification to provide 0.041 g of an intermediate. To the intermediate were added 1.0 ml of diethyl ether, 1.0 ml of water, and two drops of sodium hydroxide 5N aqueous solution, and the resultant mixture was stirred for 30.5 hours at room temperature. After adding water, the resultant mixture was subjected to extraction with diethyl ether, and the organic phase was dried with sodium sulfate. The dried organic phase was subsequently concentrated and subjected to column purification to provide 0.01 g (0.03 mmol) of the objective substance with a yield of 1.7%. Analysis results of the obtained objective substance are as follows.

$^1$H NMR (400 MHz, CDCl$_3$) δ ppm: 8.64 (d, J=5.2 Hz, 1H), 8.30 (d, J=1.6 Hz, 1H), 7.25 (dd, J=5.6, 2.0 Hz, 1H), 4.29 (s, 3H), 2.58 (s, 3H). APCIMS m/z=320.9

Example 15

Manufacturing of 6-fluoro-4-methoxy-2-(4-methoxycarbonyl-2-pyridyl)-5-trifluoromethylpyrimidine To 0.3 g (1.5 mmol) of 4-(methoxycarbonyl)pyridine-2-carboximidamide hydrochloride were added 2.3 ml of water, 0.5 g (4.9 mmol) of triethylamine (hydrogen halide-trapping agent), and 0.3 g (1.4 mmol) of 1,3,3,3-tetrafluoro-1-methoxy-2-trifluoromethyl-1-propene dissolved in 2.3 ml of acetonitrile, and the resultant mixture was stirred for 16.5 hours at room temperature. The reaction liquid was subjected to vacuum concentration and column purification to provide 0.04 g (0.01 mmol) of the objective substance with a yield of 9.3%. Analysis results of the obtained objective substance are as follows.

$^1$H NMR (400 MHz, CDCl$_3$) δ ppm: 9.030 (dd, J=5.2, 1.2 Hz, 1H), 8.99 (dd, J=1.6, 1.2 Hz, 1H), 8.03 (dd, J=4.8, 1.2 Hz, 1H), 4.32 (s, 3H), 4.03 (s, 3H). APCIMS m/z=332.7

Example 16

Manufacturing of 6-fluoro-4-methoxy-2-(2-pyrazyl)-5-trifluoromethylpyrimidine

To 75 g of dichloromethane and 75 g of water were added 25 g (0.2 mol) of 2-amidinopyrazine hydrochloride and 25 g (0.12 mol) of 1,3,3,3-tetrafluoro-1-methoxy-2-trifluoromethyl-1-propene under cooling with iced water to obtain a solution. Subsequently, 94 ml (0.45 mol) of sodium hydroxide 5N aqueous solution (hydrogen halide-trapping agent) was dropped to the solution so that the internal temperature thereof did not exceed 10° C., and the solution was heated to room temperature. After a lapse of about 12 hours, the dichloromethane phase was collected, and dichloromethane was distilled away under reduced pressure. The precipitate was dissolved in hexane followed by column purification to provide 3.5 g of the objective substance with an isolated yield of 11%. Analysis results of the obtained objective substance are as follows.

Mass spectrum (APCI, m/z): 275 ([M+H]$^+$)

$^1$H NMR (300 MHz, CDCl$_3$) δ ppm: 9.90 (d, 1H), 9.01 (m, 2H), 4.60 (s, 3H)

$^{19}$F NMR (300 MHz, C$_6$F$_6$) δ ppm: −58.75 (d, 3F), −59.29 (dd, 1F).

Example 17

Manufacturing of 6-fluoro-4-methoxy-2-(2-pyrimidyl)-5-trifluoromethylpyrimidine

To 75 g of dichloromethane and 75 g of water were added 10 g (63 mmol) of 2-amidinopyrimidine hydrochloride and 8 g (37 mmol) of 1,3,3,3-tetrafluoro-1-methoxy-2-trifluoromethyl-1-propene under cooling with iced water to obtain a solution. Subsequently, 32 ml (150 mmol) of sodium hydroxide 5N aqueous solution (hydrogen halide-trapping agent) was dropped to the solution so that the internal temperature thereof did not exceed 10° C., and the solution was heated to room temperature. After a lapse of about 12 hours, the dichloromethane phase was collected, and dichloromethane was distilled away under reduced pressure. The precipitate was dissolved in hexane followed by column purification to provide 1.2 g of the objective substance with an isolated yield of 12%. Analysis results of the obtained objective substance are as follows.

Mass spectrum (APCI, m/z): 275 ([M+H]$^+$)

$^1$H NMR (300 MHz, CDCl$_3$) δ ppm: 9.06 (dd, 2H), 7.53 (dd, 2H), 4.34 (s, 3H)

$^{19}$F NMR (300 MHz, C$_6$F$_6$) δ ppm: −58.94 (d, 3F), −59.55 (dd, 1F).

Example 18

Manufacturing of 6-fluoro-4-methoxy-2-(6-trifluoromethyl-3-pyridyl)-5-trifluoromethylpyrimidine To 3.0 ml of diethyl ether and 3.0 ml of water were added 0.5 g (2.3 mmol) of 6-(trifluoromethyl)pyridine-3-carboximidamide hydrochloride and 0.7 g (3.3 mmol) of 1,3,3,3-tetrafluoro-1-methoxy-2-trifluoromethyl-1-propene to obtain solution 1. Subsequently, 2.0 g (10.0 mmol) of sodium hydroxide 5N aqueous solution (hydrogen halide-trapping agent) was added to solution 1, and solution 1 was stirred for one day. Then, after adding water, solution 1 was subjected to extraction with diethyl ether, and the organic phase was dried with sodium sulfate. The organic phase was subsequently concentrated and subjected to column purification to provide 0.58 g (1.70 mmol) of the objective substance. A yield of the objective substance was 73.2%.

The reaction to obtain 6-fluoro-4-methoxy-2-(6-trifluoromethyl-3-pyridyl)-5-trifluoromethylpyrimidine by reacting 6-(trifluoromethyl)pyridine-3-carboximidamide hydrochloride is shown below.

[Formula 39]

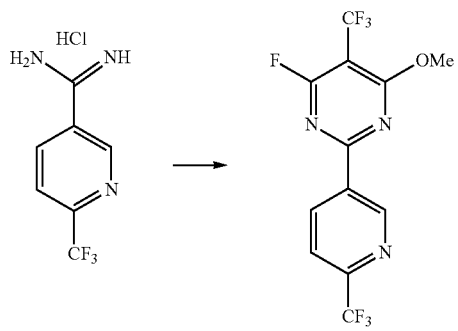

Analysis results of the obtained objective substance are as follows.

Mass spectrum (APCI, m/z): 342.5 ([M+H]$^+$)

$^1$H NMR (400 MHz, CDCl$_3$) δ 9.44 (d, J=2.0 Hz, 1H), 8.85 (dd, J=1.6, 8.4 Hz, 1H), 7.84 (dd, J=0.4, 8.0 Hz, 1H), 4.27 (s, 3H).

Example 19

Manufacturing of 6-fluoro-4-methoxy-2-(6-n-propyl-2-pyridyl)-5-trifluoromethylpyrimidine After dissolving 0.5 g (2.50 mmol) of 6-n-propyl-2-picolinamidine hydrochloride in 25 ml of acetonitrile, 0.7 g (3.30 mmol) of 1,3,3,3-tetrafluoro-1-methoxy-2-trifluoromethyl-1-propene and 1.7 g (13.1 mmol) of N,N-diisopropylethylamine (hydrogen halide-trapping agent) were added thereto, and the resultant mixture was stirred for 16.5 hours at room temperature to obtain a reaction liquid. Thereafter, the reaction liquid was subjected to column purification to provide 0.31 g (0.98 mmol) of the objective substance. A yield of the objective substance was 39%.

The reaction to obtain 6-fluoro-4-methoxy-2-(6-n-propyl-2-pyridyl)-5-trifluoromethylpyrimidine by reacting 6-n-propyl-2-picolinamidine hydrochloride is shown below.

[Formula 40]

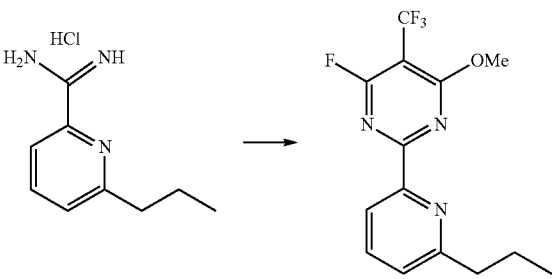

Analysis results of the obtained objective substance are as follows.

Mass spectrum (APCI, m/z): 316.2 ([M+H]$^+$)

$^1$H NMR (400 MHz, CDCl$_3$) δ 8.28: (d, J=8.0 Hz, 1H), 7.79 (t, J=7.6 Hz, 1H), 7.35 (d, J=8.0 Hz, 1H), 4.27 (s 3H), 2.94 (m, 2H), 1.83 (tq, J=7.6, 7.6 Hz, 2H), 1.02 (t, J=7.2 Hz, 3H).

Example 20

Manufacturing of 6-fluoro-4-methoxy-2-(3-pyridazinyl)-5-trifluoromethylpyrimidine After dissolving 0.2 g (1.5 mmol) of pyridazine-3-carboximidamide hydrochloride in 15 ml of acetonitrile, 0.4 g (1.9 mmol) of 1,3,3,3-tetrafluoro-1-methoxy-2-trifluoromethyl-1-propene and 1.0 g (7.7 mmol) of N,N-diisopropylethylamine (hydrogen halide-trapping agent) were added thereto, and the resultant mixture was stirred for 22.9 hours at room temperature to obtain a reaction liquid. Thereafter, the reaction liquid was subjected to column purification to provide 0.21 g (0.8 mmol) of the objective substance. A yield of the objective substance was 51.7%.

The reaction to obtain 6-fluoro-4-methoxy-2-(3-pyridazinyl)-5-trifluoromethylpyrimidine by reacting pyridazine-3-carboximidamide hydrochloride is shown below.

[Formula 41]

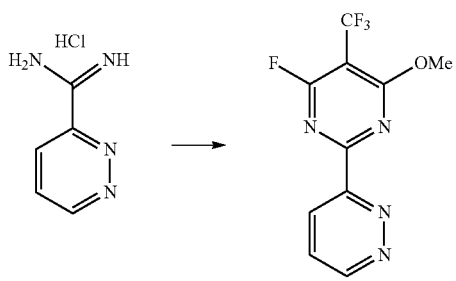

Analysis results of the obtained objective substance are as follows.

Mass spectrum (APCI, m/z): 274.6 ([M+H]$^+$)

$^1$H NMR (400 MHz, CDCl$_3$) δ 9.38 (dd, J=1.8, 4.9 Hz, 1H), 8.54 (dd, J=1.5, 8.6 Hz, 1H), 7.70 (dd, J=5.2, 8.6 Hz, 1H), 4.33 (s, 3H).

Example 21

Manufacturing of 6-fluoro-4-methoxy-2-(4-pyrimidyl)-5-trifluoromethylpyrimidine

After dissolving 0.5 g (3.2 mmol) of pyrimidine-4-carboximidamide hydrochloride in 30 ml of acetonitrile, 0.9 g (4.2 mmol) of 1,3,3,3-tetrafluoro-1-methoxy-2-trifluoromethyl-1-propene and 2.1 g (16.2 mmol) of N,N-diisopropylethylamine (hydrogen halide-trapping agent) were added thereto, and the resultant mixture was stirred for one day at room temperature to obtain a reaction liquid. Thereafter, the reaction liquid was subjected to column purification to provide 0.6 g (2.0 mmol) of the objective substance. A yield of the objective substance was 64.1%.

The reaction to obtain 6-fluoro-4-methoxy-2-(4-pyrimidyl)-5-trifluoromethylpyrimidine by reacting pyrimidine-4-carboximidamide hydrochloride is shown below.

[Formula 42]

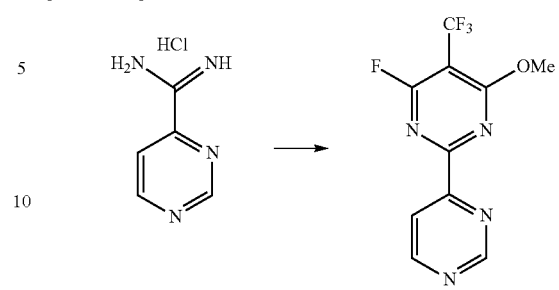

Analysis results of the obtained objective substance are as follows.

Mass spectrum (APCI, m/z): 274.8 ([M+H]$^+$)

$^1$H NMR (400 MHz, CDCl$_3$) δ 9.51 (d, J=1.2 Hz, 1H), 9.03 (d, J=5.2 Hz, 1H), 8.39 (dd, J=1.5, 5.2 Hz, 1H), 4.31 (s, 3H).

Example 22

Manufacturing of 6-fluoro-4-methoxy-2-(4-pyridazinyl)-5-trifluoromethylpyrimidine After dissolving 0.5 g (3.2 mmol) of pyridazine-4-carboximidamide hydrochloride in 30 ml of acetonitrile, 0.9 g (4.2 mmol) of 1,3,3,3-tetrafluoro-1-methoxy-2-trifluoromethyl-1-propene and 2.1 g (16.2 mmol) of N,N-diisopropylethylamine (hydrogen halide-trapping agent) were added thereto, and the resultant mixture was stirred for 23 hours at room temperature to obtain a reaction liquid. Thereafter, the reaction liquid was subjected to column purification to provide 0.4 g (1.5 mmol) of the objective substance. A yield of the objective substance was 46.5%.

The reaction to obtain 6-fluoro-4-methoxy-2-(4-pyridazinyl)-5-trifluoromethylpyrimidine by reacting pyridazine-4-carboximidamide hydrochloride is shown below.

[Formula 43]

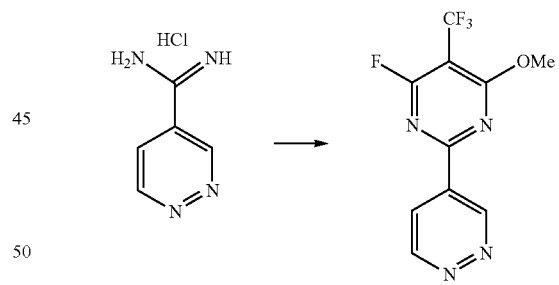

Analysis results of the obtained objective substance are as follows.

Mass spectrum (APCI, m/z): 274.9 ([M+H]$^+$)

$^1$H NMR (400 MHz, CDCl$_3$) δ 10.08 (dd, J=1.5, 2.5 Hz, 1H), 9.46 (dd, J=1.2, 5.5 Hz, 1H), 8.36 (dd, J=2.5, 5.2 Hz, 1H), 4.30 (s, 3H).

Example 23

Manufacturing of 6-fluoro-4-methoxy-2-(5-pyrimidyl)-5-trifluoromethylpyrimidine

After dissolving 0.5 g (3.2 mmol) of pyrimidine-5-carboximidamide hydrochloride in 30 ml of acetonitrile, 0.9 g (4.2 mmol) of 1,3,3,3-tetrafluoro-1-methoxy-2-trifluoromethyl-1-propene and 2.1 g (16.2 mmol) of N,N-diisopropylethylamine (hydrogen halide-trapping agent) were added thereto, and the resultant mixture was stirred for 25.6 hours at room temperature to obtain a reaction liquid. Thereafter, the reaction liquid was subjected to column purification to provide 0.4 g (1.5 mmol) of the objective substance. A yield of the objective substance was 46.6%.

The reaction to obtain 6-fluoro-4-methoxy-2-(5-pyrimidyl)-5-trifluoromethylpyrimidine by reacting pyrimidine-5-carboximidamide hydrochloride is shown below.

[Formula 44]

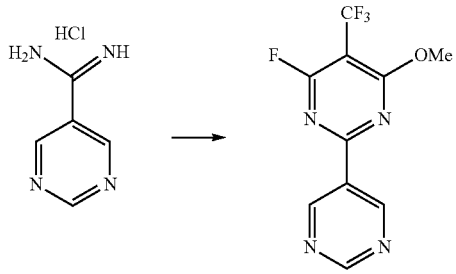

Analysis results of the obtained objective substance are as follows.

Mass spectrum (APCI, m/z): 274.7 ([M+H]$^+$)

$^1$H NMR (400 MHz, CDCl$_3$) δ 9.66 (s, 2H), 9.39 (s, 1H), 4.27 (s, 3H).

Example 24

Manufacturing of 6-fluoro-4-methoxy-2-(6-chloro-3-pyridazinyl)-5-trifluoromethylpyrimidine After dissolving 0.2 g (1.2 mmol) of 6-chloropyridazine-3-carboximidamide hydrochloride in 12 ml of acetonitrile, 0.3 g (1.4 mmol) of 1,3,3,3-tetrafluoro-1-methoxy-2-trifluoromethyl-1-propene and 0.9 g (6.9 mmol) of N,N-diisopropylethylamine (hydrogen halide-trapping agent) were added thereto, and the resultant mixture was stirred for 24.3 hours at room temperature to obtain a reaction liquid. Thereafter, the reaction liquid was subjected to column purification to provide 0.1 g of a crudely purified product of the objective substance.

The reaction to obtain 6-fluoro-4-methoxy-2-(6-chloro-3-pyridazinyl)-5-trifluoromethylpyrimidine by reacting 6-chloropyridazine-3-carboximidamide hydrochloride is shown below.

[Formula 45]

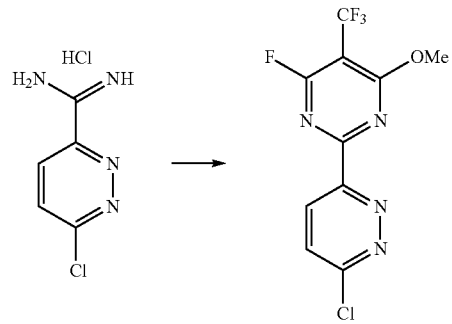

Analysis results of the obtained objective substance are as follows.

Mass spectrum (APCI, m/z): 308.6 ([M+H]$^+$)

$^1$H NMR (400 MHz, CDCl$_3$) δ 8.49 (d, J=8.9 Hz, 1H), 7.71 (d, J=8.9 Hz, 1H), 4.32 (s, 3H).

Example 25

Manufacturing of 6-fluoro-4-methoxy-2-(5-chloro-3-pyrazyl)-5-trifluoromethylpyrimidine After dissolving 0.4 g (2.0 mmol) of 5-chloropyrazine-3-carboximidamide hydrochloride in 20 ml of acetonitrile, 0.5 g (2.4 mmol) of 1,3,3,3-tetrafluoro-1-methoxy-2-trifluoromethyl-1-propene and 1.4 g (10.8 mmol) of N,N-diisopropylethylamine (hydrogen halide-trapping agent) were added thereto, and the resultant mixture was stirred for two days at room temperature to obtain a reaction liquid. Thereafter, the reaction liquid was subjected to column purification to provide 0.1 g (0.2 mmol) of the objective substance. A yield of the objective substance was 9.5%.

The reaction to obtain 6-fluoro-4-methoxy-2-(5-chloro-3-pyrazyl)-5-trifluoromethylpyrimidine by reacting 5-chloropyrazine-3-carboximidamide hydrochloride is shown below.

[Formula 46]

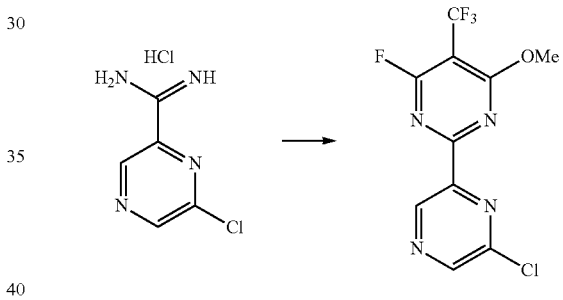

Analysis results of the obtained objective substance are as follows.

Mass spectrum (APCI, m/z): 309.6 ([M+H]$^+$)

$^1$H NMR (400 MHz, CDCl$_3$) δ 9.55 (s, 1H), 8.78 (s, 1H), 4.30 (s, 3H).

Example 26

Manufacturing of 6-fluoro-4-methoxy-2-(5-fluoro-2-pyrimidyl)-5-trifluoromethylpyrimidine After dissolving 0.2 g (1.3 mmol) of 5-fluoropyrimidine-2-carboximidamide hydrochloride in 13 ml of acetonitrile, 0.4 g (1.9 mmol) of 1,3,3,3-tetrafluoro-1-methoxy-2-trifluoromethyl-1-propene and 0.9 g (7.0 mmol) of N,N-diisopropylethylamine (hydrogen halide-trapping agent) were added thereto, and the resultant mixture was stirred for 42.4 hours at room temperature to obtain a reaction liquid. Thereafter, the reaction liquid was subjected to column purification to provide 0.02 g of a crudely purified product of the objective substance.

The reaction to obtain 6-fluoro-4-methoxy-2-(5-fluoro-2-pyrimidyl)-5-trifluoromethylpyrimidine by reacting 5-fluoropyrimidine-2-carboximidamide hydrochloride is shown below.

[Formula 47]

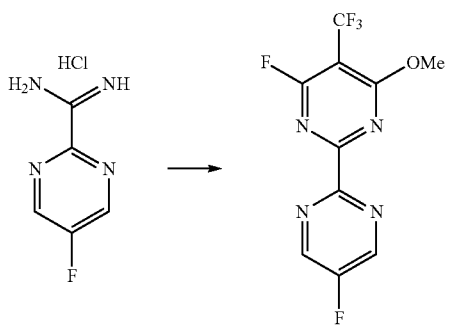

Analysis results of the obtained objective substance are as follows.
Mass spectrum (APCI, m/z): 292.6 ([M+H]$^+$)
$^1$H NMR (400 MHz, CDCl$_3$) δ 8.87 (s, 2H), 3.32 (s, 3H).

Example 27

Manufacturing of 6-fluoro-4-methoxy-2-(5-bromo-2-pyrimidyl)-5-trifluoromethylpyrimidine After dissolving 0.4 g (1.53 mmol) of 5-bromopyrimidine-2-carboximidamide hydrochloride in 15 ml of acetonitrile, 0.4 g (1.89 mmol) of 1,3,3,3-tetrafluoro-1-methoxy-2-trifluoromethyl-1-propene and 1.0 g (7.74 mmol) of N,N-diisopropylethylamine (hydrogen halide-trapping agent) were added thereto, and the resultant mixture was stirred for 38.3 hours at room temperature to obtain a reaction liquid. Thereafter, the reaction liquid was subjected to column purification to provide 0.31 g (0.87 mmol) of the objective substance. A yield of the objective substance was 56.7%.

The reaction to obtain 6-fluoro-4-methoxy-2-(5-bromo-2-pyrimidyl)-5-trifluoromethylpyrimidine by reacting 5-bromopyrimidine-2-carboximidamide hydrochloride is shown below.

[Formula 48]

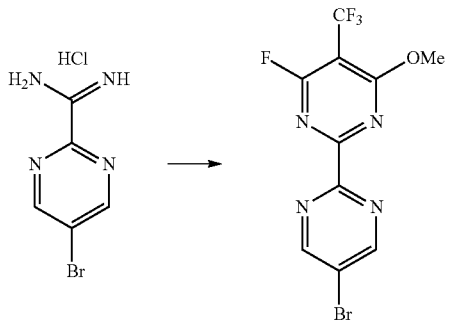

Analysis results of the obtained objective substance are as follows.
Mass spectrum (APCI, m/z): 353.6 ([M+H]$^+$)
$^1$H NMR (400 MHz, CDCl$_3$) δ 9.07 (s, 2H), 4.31 (s, 3H).

Example 28

Manufacturing of 6-fluoro-4-methoxy-2-(4-methyl-2-pyrimidyl)-5-trifluoromethylpyrimidine After dissolving 0.5 g (2.9 mmol) of 4-methylpyrimidine-2-carboximidamide hydrochloride in 30 ml of acetonitrile, 0.7 g (3.3 mmol) of 1,3,3,3-tetrafluoro-1-methoxy-2-trifluoromethyl-1-propene and 2.0 g (14.7 mmol) of N,N-diisopropylethylamine (hydrogen halide-trapping agent) were added thereto, and the resultant mixture was stirred for 28 hours at room temperature to obtain a reaction liquid. Thereafter, the reaction liquid was subjected to column purification to provide 0.6 g (2.1 mmol) of the objective substance. A yield of the objective substance was 69.7%.

The reaction to obtain 6-fluoro-4-methoxy-2-(4-methyl-2-pyrimidyl)-5-trifluoromethylpyrimidine by reacting 4-methylpyrimidine-2-carboximidamide hydrochloride is shown below.

[Formula 49]

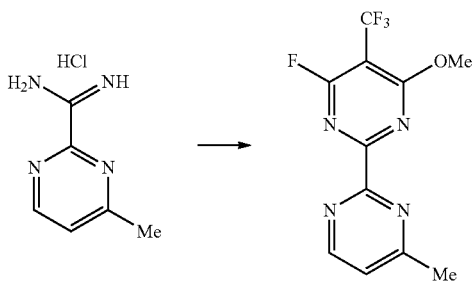

Analysis results of the obtained objective substance are as follows.
Mass spectrum (APCI, m/z): 289.2 ([M+H]$^+$)
$^1$H NMR (400 MHz, CDCl$_3$) δ 8.85 (d, J=5.2 Hz, 1H), 7.34 (d, J=4.9 Hz, 1H), 4.32 (s, 3H), 2.72 (s, 3H).

Example 29

Manufacturing of 6-fluoro-4-methoxy-2-(5-methyl-4-pyridazinyl)-5-trifluoromethylpyrimidine After dissolving 0.5 g (2.8 mmol) of 5-methylpyrimidine-4-carboximidamide hydrochloride in 30 ml of acetonitrile, 0.7 g (3.3 mmol) of 1,3,3,3-tetrafluoro-1-methoxy-2-trifluoromethyl-1-propene and 1.9 g (14.7 mmol) of N,N-diisopropylethylamine (hydrogen halide-trapping agent) were added thereto, and the resultant mixture was stirred for 26.8 hours at room temperature to obtain a reaction liquid. Thereafter, the reaction liquid was subjected to column purification to provide 0.3 g (1.2 mmol) of the objective substance. A yield of the objective substance was 41.7%.

The reaction to obtain 6-fluoro-4-methoxy-2-(5-methyl-4-pyridazinyl)-5-trifluoromethylpyrimidine by reacting 5-methylpyrimidine-4-carboximidamide hydrochloride is shown below.

[Formula 50]

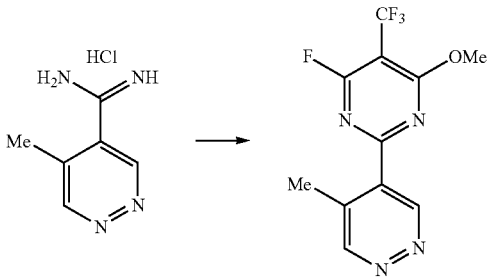

Analysis results of the obtained objective substance are as follows.

Mass spectrum (APCI, m/z): 289.0 ([M+H]$^+$)

$^1$H NMR (400 MHz, CDCl$_3$) δ 9.77 (s, 1H), 9.21 (s, 1H), 4.25 (s, 3H), 2.78 (s, 3H).

Example 30

Manufacturing of 6-fluoro-4-methoxy-2-(4-trifluoromethyl-5-pyrimidyl)-5-trifluoromethylpyrimidine After dissolving 0.2 g (1.06 mmol) of 4-(trifluoromethyl)pyrimidine-5-carboximidamide hydrochloride in 10 ml of acetonitrile, 0.3 g (1.42 mmol) of 1,3,3,3-tetrafluoro-1-methoxy-2-trifluoromethyl-1-propene and 0.7 g (5.42 mmol) of N,N-diisopropylethylamine (hydrogen halide-trapping agent) were added thereto, and the resultant mixture was stirred for 46.7 hours at room temperature to obtain a reaction liquid. Thereafter, the reaction liquid was subjected to column purification to provide 0.04 g (0.12 mmol) of the objective substance. A yield of the objective substance was 12.2%.

The reaction to obtain 6-fluoro-4-methoxy-2-(4-trifluoromethyl-5-pyrimidyl)-5-trifluoromethylpyrimidine by reacting 4-(trifluoromethyl)pyrimidine-5-carboximidamide hydrochloride is shown below.

[Formula 51]

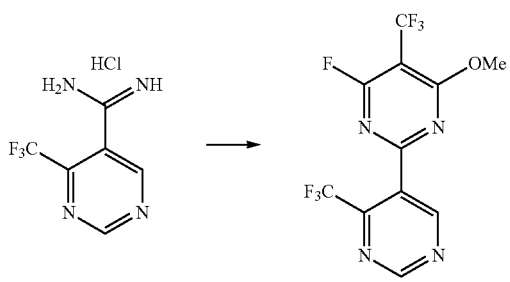

Analysis results of the obtained objective substance are as follows.

Mass spectrum (APCI, m/z): 342.4 ([M+H]$^+$)

$^1$H NMR (400 MHz, CDCl$_3$) δ 9.42 (s, 1H), 9.35 (s, 1H), 7.35 (d, J=8.0 Hz, 1H), 4.13 (s, 3H).

Example 31

Manufacturing of 6-fluoro-4-methoxy-2-(2-methylsulfanyl-5-pyrimidyl)-5-trifluoromethylpyrimidine After dissolving 0.6 g (2.9 mmol) of 2-(methylsulfanyl)pyrimidine-5-carboximidamide hydrochloride in 30 ml of acetonitrile, 0.7 g (3.3 mmol) of 1,3,3,3-tetrafluoro-1-methoxy-2-trifluoromethyl-1-propene and 1.9 g (14.7 mmol) of N,N-diisopropylethylamine (hydrogen halide-trapping agent) were added thereto, and the resultant mixture was stirred for 24.5 hours at room temperature to obtain a reaction liquid. Thereafter, the reaction liquid was subjected to column purification to provide 0.5 g (1.3 mmol) of the objective substance. A yield of the objective substance was 57.7%.

The reaction to obtain 6-fluoro-4-methoxy-2-(2-methylsulfanyl-5-pyrimidyl)-5-trifluoromethylpyrimidine by reacting 2-(methylsulfanyl)pyrimidine-5-carboximidamide hydrochloride is shown below.

[Formula 52]

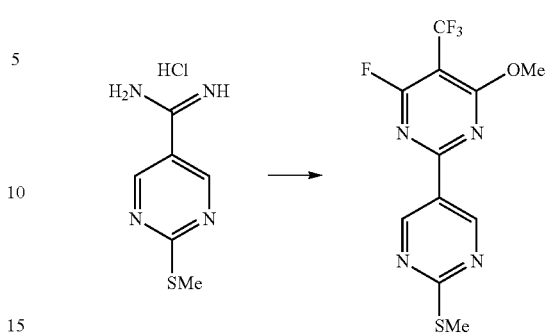

Analysis results of the obtained objective substance are as follows.

Mass spectrum (APCI, m/z): 321.0 ([M+H]$^+$)

$^1$H NMR (400 MHz, CDCl$_3$) δ 9.46 (s, 2H), 4.23 (s, 3H), 4.13 (s, 3H).

Example 32

Manufacturing of 6-fluoro-4-methoxy-2-(2-dimethylamino-5-pyrimidyl)-5-trifluoromethylpyrimidine After dissolving 0.3 g of crudely purified 2-(dimethylamino)pyrimidine-5-carboximidamide hydrochloride in 16 ml of acetonitrile, 0.5 g (2.3 mmol) of 1,3,3,3-tetrafluoro-1-methoxy-2-trifluoromethyl-1-propene and 1.1 g (8.5 mmol) of N,N-diisopropylethylamine (hydrogen halide-trapping agent) were added thereto, and the resultant mixture was stirred for 27.5 hours at room temperature to obtain a reaction liquid. Thereafter, the reaction liquid was subjected to column purification to provide 0.2 g of a crudely purified product of the objective substance.

The reaction to obtain 6-fluoro-4-methoxy-2-(2-dimethylamino-5-pyrimidyl)-5-trifluoromethylpyrimidine by reacting 2-(dimethylamino)pyrimidine-5-carboximidamide hydrochloride is shown below.

[Formula 53]

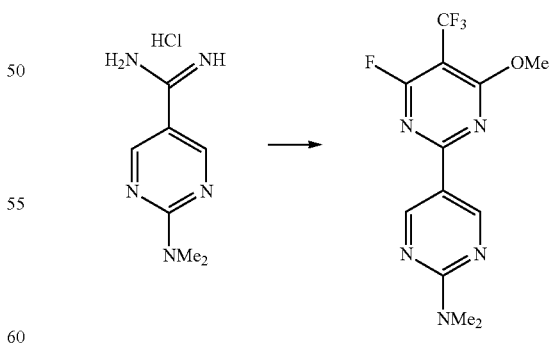

Analysis results of the obtained objective substance are as follows.

Mass spectrum (APCI, m/z): 317.9 ([M+H]$^+$)

$^1$H NMR (400 MHz, CDCl$_3$) δ 9.24 (s, 2H), 4.17 (s, 3H), 3.31 (s, 6H).

Example 33

Manufacturing of 6-fluoro-4-methoxy-2-(6-methoxy-4-pyrimidyl)-5-trifluoromethylpyrimidine After dissolving 0.6 g (3.3 mmol) of 6-methoxypyrimidine-4-carboximidamide hydrochloride in 33 ml of acetonitrile, 0.9 g (4.2 mmol) of 1,3,3,3-tetrafluoro-1-methoxy-2-trifluoromethyl-1-propene and 2.3 g (17.8 mmol) of N,N-diisopropylethylamine (hydrogen halide-trapping agent) were added thereto, and the resultant mixture was stirred for one day at room temperature to obtain a reaction liquid. Thereafter, the reaction liquid was subjected to column purification to provide 0.7 g (2.2 mmol) of the objective substance.

The reaction to obtain 6-fluoro-4-methoxy-2-(6-methoxy-4-pyrimidyl)-5-trifluoromethylpyrimidine by reacting 6-methoxypyrimidine-4-carboximidamide hydrochloride is shown below.

[Formula 54]

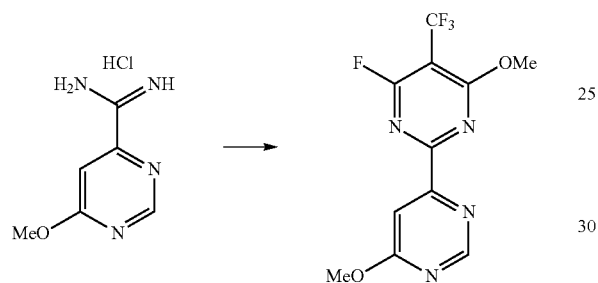

Analysis results of the obtained objective substance are as follows.

Mass spectrum (APCI, m/z): 304.6 ([M+H]$^+$)

$^1$H NMR (400 MHz, CDCl$_3$) δ 9.01 (d, J=0.9 Hz, 1H), 7.80 (d, J=1.1 Hz, 1H), 4.28 (s, 3H), 4.09 (s, 3H).

(Evaluation Test on Rice Blast)

An acetone solution in which 6-fluoro-4-methoxy-2-(2-pyridyl)-5-trifluoromethylpyrimidine prepared in Example 3 is diluted to a concentration of 500 ppm was prepared, and an oatmeal medium, which was separately prepared, was treated by dropping 1000 μl of the acetone solution thereon and air dried. Thereafter, a rice blast disc having a size of 8 mm was placed so that bacterial flora contacted the treated surface of the oatmeal medium. Thereafter, the oatmeal medium was allowed to stand still in a thermostatic chamber at 25° C. for five days, and elongation lengths of fungal filaments were subsequently examined. A preventive value calculated according to the following formula was 80.

Preventive value={(average fungal filament elongation length without treatment−average fungal filament elongation length after treatment)/average fungal filament elongation length without treatment}×100

Incidentally, the phrase "without treatment" in the above formula indicates that a medium was treated by dropping only acetone thereon as a test liquid.

The phrase "after treatment" indicates that a medium was treated by dropping a test liquid in which a specimen was subjected to dilution adjustment treatment with acetone to have a predetermined concentration.

The invention claimed is:

1. A fluorine-containing pyrimidine compound represented by a general formula (1), (2), (3), (4), (5), or (6) below:

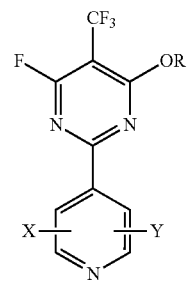

(1)

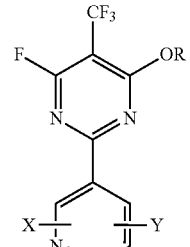

(2)

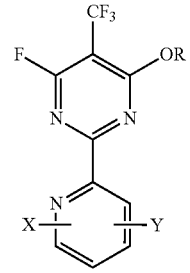

(3)

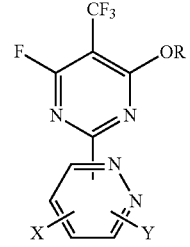

(4)

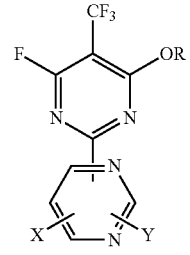

(5)

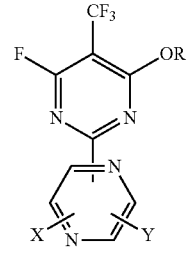

(6)

wherein, in the general formulae (1) to (6) above,

R represents a hydrocarbon group having 1 to 12 carbon atoms, and

X and Y each independently represent a hydrogen atom, a halogen atom, a hydrocarbon group having 1 to 10 carbon atoms, —$C_nF_{2n+1}$ (n is an integer of 1 to 10), a nitro group, a boronate group, —$OA^1$, —$SO_mA^1$ (m is an integer of 0 to 3), —$NA^1A^2$, —$COOA^1$, or —$CONA^1A^2$, and $A^1$ and $A^2$ each independently represent a hydrogen atom or a hydrocarbon group having 1 to 10 carbon atoms.

2. The fluorine-containing pyrimidine compound according to claim 1, wherein the R is an alkyl group having 1 to 10 carbon atoms.

3. A method for manufacturing a fluorine-containing pyrimidine compound, comprising:

(a) reacting a fluoroisobutylene derivative represented by a general formula (7) below with a compound represented by a general formula (8) below or a salt thereof to provide a fluorine-containing pyrimidine compound of a general formula (1) below,

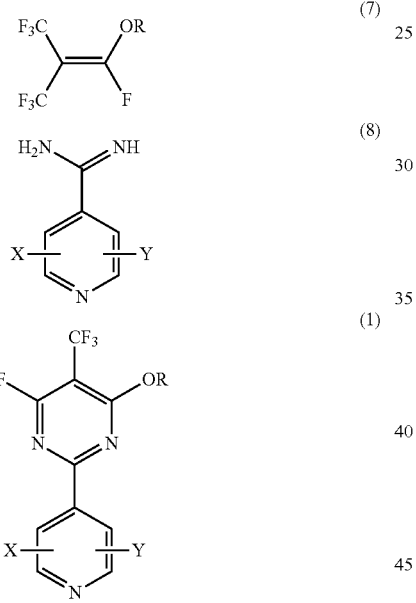

(b) reacting a fluoroisobutylene derivative represented by a general formula (7) below with a compound represented by a general formula (9) below or a salt thereof to provide a fluorine-containing pyrimidine compound of a general formula (2) below,

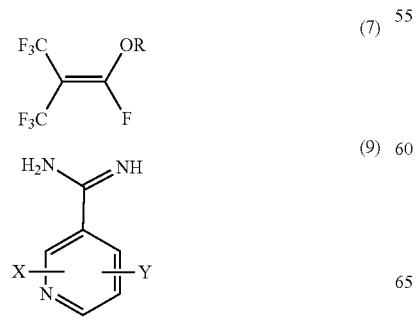

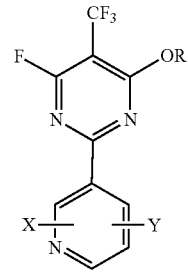

(c) reacting a fluoroisobutylene derivative represented by a general formula (7) below with a compound represented by a general formula (10) below or a salt thereof to provide a fluorine-containing pyrimidine compound of a general formula (3) below,

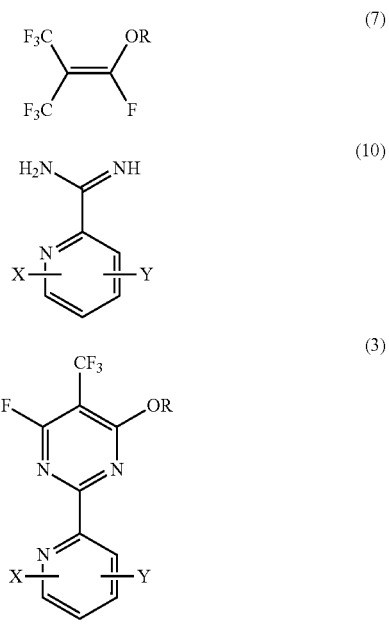

(d) reacting a fluoroisobutylene derivative represented by a general formula (7) below with a compound represented by a general formula (11) below or a salt thereof to provide a fluorine-containing pyrimidine compound of a general formula (4) below,

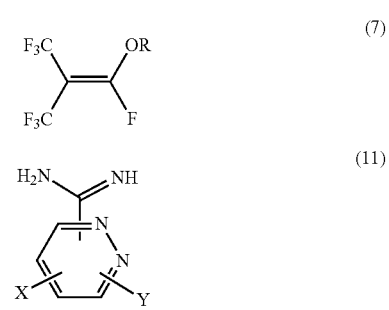

-continued

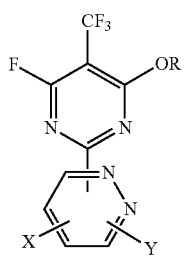
(4)

(e) reacting a fluoroisobutylene derivative represented by a general formula (7) below with a compound represented by a general formula (12) below or a salt thereof to provide a fluorine-containing pyrimidine compound of a general formula (5) below,

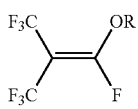
(7)

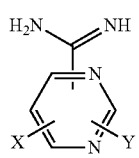
(12)

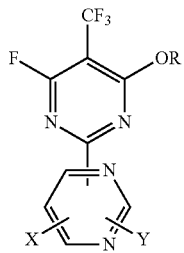
(5)

or (f) reacting a fluoroisobutylene derivative represented by a general formula (7) below with a compound represented by a general formula (13) below or a salt thereof to provide a fluorine-containing pyrimidine compound of a general formula (6) below,

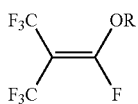
(7)

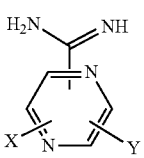
(13)

-continued

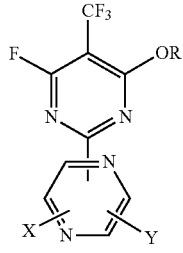
(6)

wherein, in the general formulae (1) to (13) above,

R represents a hydrocarbon group having 1 to 12 carbon atoms, and

X and Y each independently represent a hydrogen atom, a halogen atom, a hydrocarbon group having 1 to 10 carbon atoms, $-C_nF_{2n+1}$ (n is an integer of 1 to 10), a nitro group, a boronate group, $-OA^1$, $-SO_mA^1$ (m is an integer of 0 to 3), $-NA^1A^2$, $-COOA^1$, or $-CONA^1A^2$, and $A^1$ and $A^2$ each independently represent a hydrogen atom or a hydrocarbon group having 1 to 10 carbon atoms.

4. A method for manufacturing a fluorine-containing pyrimidine compound, comprising:

(g) reacting a fluoroisobutane derivative represented by a general formula (14) below with a compound represented by a general formula (8) below or a salt thereof to provide a fluorine-containing pyrimidine compound of a general formula (1) below,

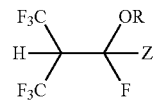
(14)

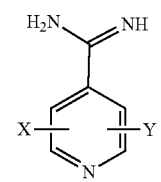
(8)

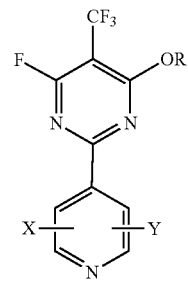
(1)

(h) reacting a fluoroisobutane derivative represented by a general formula (14) below with a compound represented by a general formula (9) below or a salt thereof to provide a fluorine-containing pyrimidine compound of a general formula (2) below,

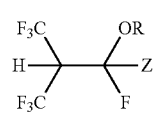
(14)

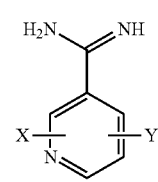
(9)

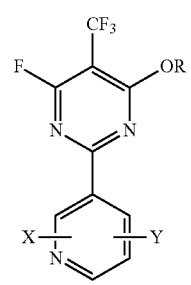
(2)

(i) reacting a fluoroisobutane derivative represented by a general formula (14) below with a compound represented by a general formula (10) below or a salt thereof to provide a fluorine-containing pyrimidine compound of a general formula (3) below,

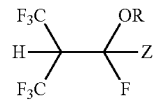
(14)

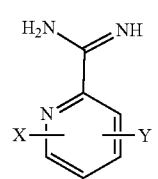
(10)

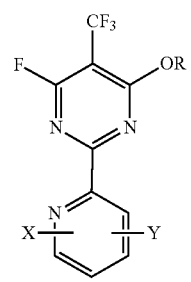
(3)

(j) reacting a fluoroisobutane derivative represented by a general formula (14) below with a compound represented by a general formula (11) below or a salt thereof to provide a fluorine-containing pyrimidine compound of a general formula (4) below,

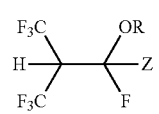
(14)

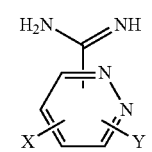
(11)

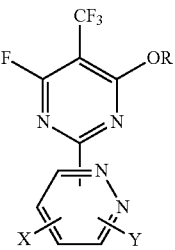
(4)

(k) reacting a fluoroisobutane derivative represented by a general formula (14) below with a compound represented by a general formula (12) below or a salt thereof to provide a fluorine-containing pyrimidine compound of a general formula (5) below,

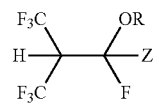
(14)

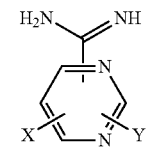
(12)

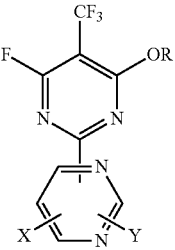
(5)

or (l) reacting a fluoroisobutane derivative represented by a general formula (14) below with a compound represented by a general formula (13) below or a salt thereof to provide a fluorine-containing pyrimidine compound of a general formula (6) below,

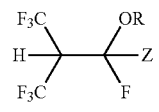
(14)

-continued

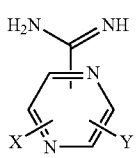
(13)

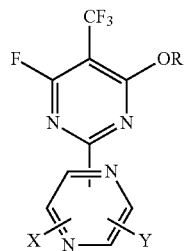
(6)

wherein, in the general formulae (1) to (6) and (8) to (14) above,

R represents a hydrocarbon group having 1 to 12 carbon atoms,

X and Y each independently represent a hydrogen atom, a halogen atom, a hydrocarbon group having 1 to 10 carbon atoms, —$C_nF_{2n+1}$ (n is an integer of 1 to 10), a nitro group, a boronate group, —$OA^1$, —$SO_mA^1$ (m is an integer of 0 to 3), —$NA^1A^2$, —$COOA^1$, or —$CONA^1A^2$, Z represents a halogen atom, —$OA^1$, —$SO_mA^1$ (m is an integer of 0 to 3), or —$NA^1A^2$, and $A^1$ and $A^2$ each independently represent a hydrogen atom or a hydrocarbon group having 1 to 10 carbon atoms.

5. The method for manufacturing a fluorine-containing pyrimidine compound according to claim 3, wherein the R is an alkyl group having 1 to 10 carbon atoms.

6. The method for manufacturing a fluorine-containing pyrimidine compound according to claim 4, wherein the R is an alkyl group having 1 to 10 carbon atoms.

* * * * *